United States Patent
Beavers et al.

(10) Patent No.: US 8,008,296 B2
(45) Date of Patent: Aug. 30, 2011

(54) HISTAMINE H3 RECEPTOR AGENTS, PREPARATION AND THERAPEUTIC USES

(75) Inventors: Lisa Selsam Beavers, Franklin, IN (US); Don Richard Finley, Greenwood, IN (US); Robert Alan Gadski, Indianapolis, IN (US); Philip Arthur Hipskind, New Palestine, IN (US); William Joseph Hornback, Fishers, IN (US); Cynthia Darshini Jesudason, Indianapolis, IN (US); Richard Todd Pickard, Noblesville, IN (US); Takako Takakuwa, Indianapolis, IN (US); Grant Mathews Vaught, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 715 days.

(21) Appl. No.: 11/917,941

(22) PCT Filed: Jun. 28, 2006

(86) PCT No.: PCT/US2006/025328
§ 371 (c)(1),
(2), (4) Date: Dec. 18, 2007

(87) PCT Pub. No.: WO2007/005503
PCT Pub. Date: Jan. 11, 2007

(65) Prior Publication Data
US 2010/0160319 A1  Jun. 24, 2010

Related U.S. Application Data

(60) Provisional application No. 60/696,257, filed on Jul. 1, 2005.

(51) Int. Cl.
| | |
|---|---|
| *A61K 31/535* | (2006.01) |
| *A61K 31/497* | (2006.01) |
| *A61K 31/445* | (2006.01) |
| *C07D 413/00* | (2006.01) |
| *C07D 409/00* | (2006.01) |
| *C07D 207/00* | (2006.01) |

(52) U.S. Cl. ............... 514/235.5; 514/254.01; 514/326; 514/422; 544/141; 544/372; 546/208; 548/523

(58) Field of Classification Search .................. None
See application file for complete search history.

(56) References Cited

FOREIGN PATENT DOCUMENTS

| | | |
|---|---|---|
| WO | WO 02/076925 A2 | 10/2002 |
| WO | WO 03/064411 A1 | 8/2003 |
| WO | WO 2004/037251 A1 | 5/2004 |
| WO | WO 2005/097740 * | 10/2005 |
| WO | WO 2006/011042 A1 | 2/2006 |

* cited by examiner

*Primary Examiner* — Brandon Fetterolf
*Assistant Examiner* — Anna Pagonakis
(74) *Attorney, Agent, or Firm* — Dan L. Wood

(57) ABSTRACT

The present invention discloses novel compounds of Formula I or pharmaceutically acceptable salts thereof which have histamine-H3 receptor antagonist or inverse agonist activity, as well as methods for preparing such compounds. In another embodiment, the invention discloses pharmaceutical compositions comprising compounds of Formula I as well as methods of using them to treat obesity, cognitive deficiencies, narcolepsy, and other histamine H3 receptor-related diseases. (Formula I).

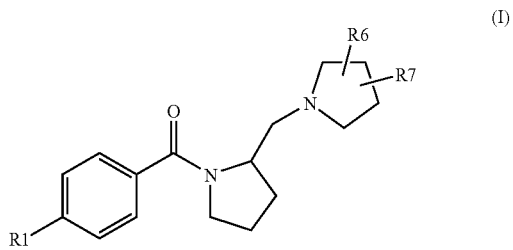

11 Claims, No Drawings

HISTAMINE H3 RECEPTOR AGENTS, PREPARATION AND THERAPEUTIC USES

This is the national phase application, under 35 USC 371, for PCT/US2006/025328, filed Jun. 28, 2006, which claims the benefit, under 35 USC 119(e), of US provisional application 60/696,257 filed Jul. 1, 2005.

The present invention relates to novel aryl-methanone-pyrrolidinyl-methyl-pyrrolidinyl compounds, to pharmaceutical compositions comprising the compounds, to methods of treatment employing these compounds and compositions, and to intermediates and methods for making these compounds.

The histamine H3 receptor is relatively neuron specific and inhibits the release of a number of monoamines, including histamine. The histamine H3 receptor is a presynaptic autoreceptor and hetero-receptor located both in the central and the peripheral nervous system. The histamine H3 receptor regulates the release of histamine and other neurotransmitters, such as serotonin and acetylcholine. These are examples of histamine H3 receptor mediated responses. Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-regulated neurotransmitters in the brain. A histamine H3 receptor agonist, on the contrary, leads to an inhibition of the biosynthesis and or release of histamine, and other neurotransmitters, such as serotonin and acetylcholine. These findings suggest that histamine H3 receptor agonists, inverse agonists, and antagonists could be important mediators of neuronal activity, and the activities of other cells that may express this receptor. Inverse agonism or selective antagonism of the histamine H3 receptor raises brain levels of histamine, and other monoamines, and inhibits activities such as food consumption while minimizing non-specific peripheral consequences. By this mechanism, they induce a prolonged wakefulness, improved cognitive function, reduction in food intake, and normalization of vestibular reflexes. Accordingly, the histamine H3 receptor is an important target for new therapeutics in Alzheimers disease, mood and attention adjustments, cognitive deficiencies, obesity, dizziness, schizophrenia, epilepsy, sleeping disorders, narcolepsy and motion sickness.

Histamine mediates its activity via four receptor subtypes, H1R, H2R, H3R and a newly identified receptor designated GPRv53 [(Oda T., et al., J. Biol. Chem. 275 (47): 36781-6 (2000)]. Alternative names for GPRv53 are PORT3 or H4R. Although relatively selective ligands have been developed for H1R, H2R and H3R, few specific ligands have been developed that can distinguish H3R from H4R. H4R is a widely distributed receptor found at high levels in human leukocytes. Activation or inhibition of this receptor could result in undesirable side effects when targeting antagonism of the H3R receptor. The identification of the H4R receptor has fundamentally changed histamine biology and must be considered in the development of histamine H3 receptor antagonists.

Some histamine H3 receptor antagonists were created which resembled histamine in possessing an imidazole ring generally substituted in the 4(5) position (Ganellin et al., Ars Pharmaceutica, 1995, 36:3, 455-468). These imidazole-containing compounds have the disadvantage of poor blood-brain barrier penetration, interaction with cytochrome P-450 proteins, and hepatic and ocular toxicities. Recently other imidazole and non-imidazole ligands of the histamine H3 receptor have been described, such as those of WO 2002076925.

There remains a need for improved treatments using alternative or improved pharmaceutical agents that act as histamine H3 receptor agonists, inverse agonists, or antagonists, to modulate H3 receptor activity, and treat the diseases that could benefit from H3 receptor modulation. The present invention provides such a contribution to the art based on the finding that a novel class of aryl-methanone-pyrrolidinyl-methyl-pyrrolidinyl compounds has a high affinity, selective, and potent activity at the histamine H3 receptor. The subject invention is distinct in the particular structures and their activities.

The present invention provides a compound structurally represented by Formula I:

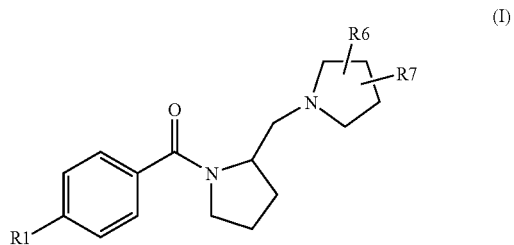

(I)

or a pharmaceutically acceptable salt thereof, wherein:

R1 is independently
—N(R2)(R3), —N(R2)SO$_2$-phenyl (wherein the phenyl is optionally substituted with R4), —N(R2)SO$_2$—CH$_2$-phenyl (wherein the phenyl is optionally substituted with R4), —N-pyrrolidinyl (wherein the pyrrolidine is optionally substituted with R4), —N-piperidinyl (wherein the piperidine is optionally substituted with R4), —N-morpholinyl, —N(R2)C(O)NH(R3), —C(O)N(R2)(R3), —SO$_2$N(R2)(R3), —SO$_2$—N-pyrrolidinyl (wherein the pyrrolidine is optionally substituted with R4), —SO$_2$—N-piperidinyl (wherein the piperidine is optionally substituted with R4), —SO$_2$—N-morpholinyl, or —X—(CH$_2$)$_n$—R5 (wherein X=—S— or —CH$_2$— and n is 0, 1, 2, 3, or 4); wherein when n is 0 then (CH$_2$)$_n$ is a bond;

R2 is independently —H or —(C$_1$-C$_4$) alkyl (optionally substituted with one to three halogens);

R3 is independently
—(C$_1$-C$_6$) alkyl(optionally substituted with one to three halogens), —(C$_2$-C$_4$) alkylene-N-pyrrolidinyl, —(C$_2$-C$_4$) alkylene-N-piperidinyl, —(C$_2$-C$_4$) alkylene-N-morpholinyl, —(C$_1$-C$_4$) alkylene-2-pyridinyl, —(C$_1$-C$_4$) alkylene-3-pyridinyl, or —(C$_1$-C$_4$) alkylene-4-pyridinyl;

R4 is independently —CH$_3$, —CF$_3$, —CN, or —SO$_2$CH$_3$;

R5 is independently
—N(R2)(C$_1$-C$_6$) alkyl, (optionally substituted with one to three halogens), —N(R2)((C$_3$-C$_7$)cycloalkyl), —N(R2)(—CH$_2$-phenyl), —N-pyrrolidinyl, —N-piperidinyl, —N-morpholinyl, —N-piperazine-N-methyl, -2-pyridinyl, -3-pyridinyl, -4-pyridinyl, -2-pyrimidinyl, or -4-pyrimidinyl, provided, however, that wherein X is —S— and n is 0 or 1, then R5 is not —N(R2)(C$_1$-C$_6$) alkyl(optionally substituted with one to three halogens), —N(R2)((C$_3$-C$_7$)cycloalkyl), —N(R2)(—CH$_2$-phenyl), —N-pyrrolidinyl, —N-piperidinyl, —N-morpholinyl, or —N-piperazine-N-methyl;

R6 is independently —H or —(C₁-C₃) alkyl(optionally substituted with one to three halogens); and R7 is independently —H or —(C₁-C₃) alkyl(optionally substituted with one to three halogens).

The present invention provides compounds that show a selective and high affinity binding for the histamine H3 receptor, and thus the compounds are useful as histamine H3 receptor antagonists or inverse agonists. In another aspect, the present invention provides compounds that are useful as selective antagonists or inverse agonists of the histamine H3 receptor but have little or no binding affinity of GPRv53. In addition, the present invention provides a method for the treatment of a nervous system disorder, which comprises administering to a patient in need thereof an effective amount of a compound of Formula I. The present invention further provides a method for the treatment of obesity or cognitive disorders, which comprises administering to a patient in need thereof an effective amount of a compound of Formula I. In yet another aspect, the present invention provides pharmaceutical compositions comprising antagonists or inverse agonists of the histamine H3 receptor.

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R. The term "H3R" means the histamine H3 receptor that inhibits the release of a number of monoamines, including histamine. The term "H1R" means the histamine H1 receptor subtype. The term "H2R" means the histamine H2 receptor subtype. The term "H3R antagonists" is defined as a compound of the present invention with the ability to block forskolin-stimulated cAMP production in response to agonist R(−)α methylhistamine. The term "H3R inverse agonist" is defined as a compound of the present invention with the ability to inhibit the constitutive activity of H3R. "Selective H3R antagonists or inverse agonists" means a compound of the present invention having a greater affinity for H3 histamine receptor than for GPRv53 histamine receptor.

In the general formulae of the present document, the general chemical terms have their usual meanings.

"(C₁-C₄) alkylene" are a saturated hydrocarbyldiyl radical of straight or branched configuration made up of from 1 to 4 carbon atoms. Included within the scope of this term are methylene, 1,2-ethane-diyl, 1,1-ethane-diyl, 1,3-propane-diyl, 1,2-propane-diyl, 1,3 butane-diyl, 1,4-butane-diyl, and the like. "(C₂-C₄) alkylene" are a saturated hydrocarbyldiyl radical of straight or branched configuration made up of from 2 to 4 carbon atoms. Included within the scope of this term are 1,2-ethane-diyl, 1,3-propane-diyl, 1,2-propane-diyl, 1,3-butane-diyl, 1,4-butane-diyl, and the like.

"(C₁-C₃) alkyl" are one to three carbon atoms such as methyl, ethyl, propyl, and the like, optionally substituted with one to three halogens, and "(C₁-C₄) alkyl" are one to four carbon atoms such as methyl, ethyl, propyl, butyl, and the like, and branched or isomeric forms thereof, optionally substituted with one to three halogens, and "(C₁-C₆) alkyl" are one to six carbon atoms such as methyl, ethyl, propyl, butyl, pentyl, hexyl, and the like, and branched or isomeric forms thereof, optionally substituted with one to three halogens.

"(C₃-C₇)cycloalkyl" means a ring with three to seven carbon atoms such as cyclopropyl, cyclobutyl, cyclopentyl, cyclohexyl, and cycloheptyl.

"—N-piperidinyl" is

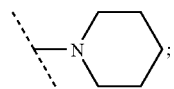

"—N-pyrrolidinyl" is

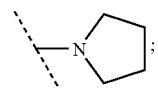

"—N-morpholinyl" is

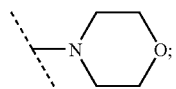

"—N-piperazine-N-methyl" is

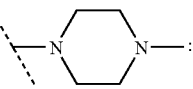

wherein the dashed lines represent the points of attachment.

"Halogen" or "halo" means fluoro, chloro, bromo and iodo.

The term "optionally substituted" as used herein means that the groups in question are either unsubstituted or substituted with one or more of the substituents specified. When the groups in question are substituted with more than one substituent, the substituents may be the same or different. Furthermore, when using the terms "independently", "independently are" and "independently selected from" it should be understood that the groups in question may be the same or different. Certain of the above defined terms may occur more than once in the structural formulae, and upon such occurrence each term shall be defined independently of the other.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The terms "treatment", "treating", and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

In general, the term "pharmaceutical" when used as an adjective means substantially non-toxic to living organisms. For example, the term "pharmaceutically acceptable salt" as used herein, refers to salts of the compounds of Formula I which are substantially non-toxic to living organisms. See, e.g., Berge, S. M, Bighley, L. D., and Monkhouse, D. C., "Pharmaceutical Salts," *J. Pharma. Sci.*, 66:1, 1977. The present invention also encompasses pharmaceutically acceptable salts of the present compounds.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

In one embodiment, the present invention provides compounds of Formula I as described in detail above. While all of the compounds of the present invention are useful, certain of the compounds are particularly interesting and are preferred.

In another embodiment the present invention provides a compound structurally represented by Formula I or a pharmaceutically acceptable salt thereof, wherein:
R1 is independently
—N(R2)(R3), —N(R2)SO$_2$-phenyl (wherein the phenyl is optionally substituted with R4), —N(R2)SO$_2$—CH$_2$-phenyl (wherein the phenyl is optionally substituted with R4), —N-pyrrolidinyl (wherein the pyrrolidine is optionally substituted with R4), —N-piperidinyl (wherein the piperidine is optionally substituted with R4), —N-morpholinyl, —N(R2)C(O)NH(R3);
R2 is independently —H or —(C$_1$-C$_4$) alkyl (optionally substituted with one to three halogens);
R3 is independently
—(C$_1$-C$_6$) alkyl(optionally substituted with one to three halogens), —(C$_2$-C$_4$) alkylene-N-pyrrolidinyl, —(C$_2$-C$_4$) alkylene-N-piperidinyl, —(C$_2$-C$_4$) alkylene-N-morpholinyl, —(C$_1$-C$_4$) alkylene-2-pyridinyl, —(C$_1$-C$_4$) alkylene-3-pyridinyl, or —(C$_1$-C$_4$) alkylene-4-pyridinyl;
R4 is independently —CH$_3$, —CF$_3$, —CN, or —SO$_2$CH$_3$;
R6 is independently —H or CH$_3$; and R7 is independently —H or CH$_3$.

In another embodiment the present invention provides a compound structurally represented by Formula I or a pharmaceutically acceptable salt thereof, wherein:
R1 is independently —C(O)N(R2)(R3);
R2 is independently —H or —(C$_1$-C$_4$) alkyl (optionally substituted with one to three halogens);
R3 is independently
—(C$_1$-C$_6$) alkyl(optionally substituted with one to three halogens), —(C$_2$-C$_4$) alkylene-N-pyrrolidinyl, —(C$_2$-C$_4$) alkylene-N-piperidinyl, —(C$_2$-C$_4$) alkylene-N-morpholinyl, —(C$_1$-C$_4$) alkylene-2-pyridinyl, —(C$_1$-C$_4$) alkylene-3-pyridinyl, or —(C$_1$-C$_4$) alkylene-4-pyridinyl;
R6 is independently —H or CH$_3$; and R7 is independently —H or CH$_3$.

In another embodiment the present invention provides a compound structurally represented by Formula I or a pharmaceutically acceptable salt thereof, wherein:
R1 is independently
—SO$_2$N(R2)(R3), —SO$_2$—N-pyrrolidinyl (wherein the pyrrolidine is optionally substituted with R4), —SO$_2$—N-piperidinyl (wherein the piperidine is optionally substituted with R4), or —SO$_2$—N-morpholinyl;
R2 is independently —H or —(C$_1$-C$_4$) alkyl (optionally substituted with one to three halogens);
R3 is independently
—(C$_1$-C$_6$) alkyl(optionally substituted with one to three halogens), —(C$_2$-C$_4$) alkylene-N-pyrrolidinyl, —(C$_2$-C$_4$) alkylene-N-piperidinyl, —(C$_2$-C$_4$) alkylene-N-morpholinyl, —(C$_1$-C$_4$) alkylene-2-pyridinyl, —(C$_1$-C$_4$) alkylene-3-pyridinyl, or —(C$_1$-C$_4$) alkylene-4-pyridinyl;
R4 is independently —CH$_3$, —CF$_3$, —CN, or —SO$_2$CH$_3$;
R6 is independently —H or CH$_3$; and R7 is independently —H or CH$_3$.

In another embodiment the present invention provides a compound structurally represented by Formula I or a pharmaceutically acceptable salt thereof, wherein:
R1 is independently
—X—(CH$_2$)$_n$—R5, wherein X=CH$_2$—, and n is 0, 1, 2, 3, or 4; wherein when n is 0 then (CH$_2$)$_n$ is a bond;
R2 is independently —H or —(C$_1$-C$_4$) alkyl (optionally substituted with one to three halogens);
R5 is independently
—N(R2)(C$_1$-C$_6$) alkyl, (optionally substituted with one to three halogens), —N(R2)((C$_3$-C$_7$)cycloalkyl), —N(R2)(—CH$_2$-phenyl), —N-pyrrolidinyl, —N-piperidinyl, —N-morpholinyl, —N-piperazine-N-methyl, -2-pyridinyl, -3-pyridinyl, -4-pyridinyl, -2-pyrimidinyl, or -4-pyrimidinyl, provided, however, that wherein X is —S— and n is 0 or 1, then R5 is not —N(R2)(C$_1$-C$_6$) alkyl(optionally substituted with one to three halogens), —N(R2)((C$_3$-C$_7$)cycloalkyl), —N(R2)(—CH$_2$-phenyl), —N-pyrrolidinyl, —N-piperidinyl, —N-morpholinyl, or —N-piperazine-N-methyl;
R6 is independently —H or —CH$_3$; and R7 is independently —H or —CH$_3$.

In another embodiment the present invention provides a compound structurally represented by Formula I or a pharmaceutically acceptable salt thereof, wherein:
R1 is independently
—X—(CH$_2$)$_n$—R5, wherein X=—S—, and n is 0, 1, 2, 3, or 4; wherein when n is 0 then (CH$_2$)$_n$ is a bond;
R2 is independently —H or —(C$_1$-C$_4$) alkyl (optionally substituted with one to three halogens);
R5 is independently
—N(R2)(C$_1$-C$_6$) alkyl, (optionally substituted with one to three halogens), —N(R2)((C$_3$-C$_7$)cycloalkyl), —N(R2) (—CH$_2$-phenyl), —N-pyrrolidinyl, —N-piperidinyl, —N-morpholinyl, —N-piperazine-N-methyl, -2-pyridinyl, -3-pyridinyl, -4-pyridinyl, -2-pyrimidinyl, or -4-pyrimidinyl, provided, however, that wherein X is —S— and n is 0 or 1, then R5 is not —N(R2)(C$_1$-C$_6$)

alkyl(optionally substituted with one to three halogens), —N(R2)((C$_3$-C$_7$)cycloalkyl), —N(R2)(—CH$_2$-phenyl), —N-pyrrolidinyl, —N-piperidinyl, —N-morpholinyl, or —N-piperazine-N-methyl;

R6 is independently —H or —CH$_3$; and R7 is independently —H or —CH$_3$.

In another embodiment the present invention is a compound structurally represented by Formula I:

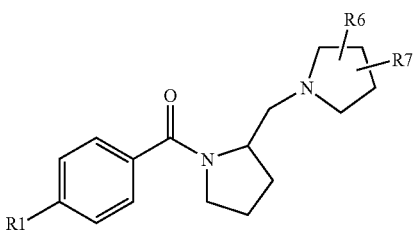

(I)

or pharmaceutically acceptable salts thereof, wherein:
R1 is independently
—N(R2)(R3), —N(R2)SO$_2$-phenyl (wherein the phenyl is optionally substituted with R4), —N(R2)SO$_2$(CH$_2$)phenyl (wherein the phenyl is optionally substituted with R4), —N-pyrollidinyl (wherein the pyrollidine is optionally substituted with R4), —N-piperidinyl (wherein the piperidine is optionally substituted with R4), —N-morpholinyl, —N(R2)C(O)NH(R3), —C(O)N(R2)(R3), —SO$_2$N(R2)(R3), —SO$_2$N-pyrollidinyl (wherein the pyrollidine is optionally substituted with R4), —SO$_2$N-piperidinyl (wherein the piperidine is optionally substituted with R4), —SO$_2$N-morpholinyl, or —X(CH$_2$)$_n$(R5) (wherein X=—S— or —CH$_2$— and n is 0, 1, 2, 3, or 4);

R2 is independently —H, or —(C$_1$-C$_4$) alkyl;
R3 is independently —(C$_1$-C$_6$) alkyl, —(C$_2$-C$_4$) alkylene-N-pyrrolidinyl, —(C$_2$-C$_4$) alkylene-N-piperidinyl, —(C$_2$-C$_4$) alkylene-N-morpholinyl, —(C$_1$-C$_4$) alkylene-2-pyridinyl, —(C$_1$-C$_4$) alkylene-3-pyridinyl, or —(C$_1$-C$_4$) alkylene-4-pyridinyl;
R4 is independently —CH$_3$, —CF$_3$, —CN, or —SO$_2$Me;
R5 is independently —N(R2)(C$_1$-C$_6$) alkyl, —N(R2)(cycloalkyl), —N(R2)(CH$_2$-phenyl), —N-pyrrolidinyl, —N-piperidinyl, —N-morpholinyl, —N-piperazine-N-methyl, -2-pyridinyl, -3-pyridinyl, -4-pyridinyl, -2-pyrimidinyl, or -4-pyrimidinyl, Provided, however, that wherein X is —S— and n is 0 or 1, then R5 is not —N(R2)(C$_1$-C$_6$) alkyl, —N(R2)(cycloalkyl), —N(R2)(CH$_2$)phenyl, —N-pyrrolidinyl, —N-piperidinyl, —N-morpholinyl, or —N-piperazine-N-methyl;
R6 is independently —H; or —(C$_1$-C$_3$) alkyl; R7 is independently —H, or —(C$_1$-C$_3$) alkyl.

Additional embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

In a preferred embodiment R1 is —N(R2)(R3), —N(R2)SO$_2$-phenyl (wherein the phenyl is optionally substituted with R4), —N(R2)SO$_2$(—CH$_2$-phenyl) (wherein the phenyl is optionally substituted with R4), —N-pyrrolidinyl (wherein the pyrrolidine is optionally substituted with R4), —N-piperidinyl (wherein the piperidine is optionally substituted with R4), —N-morpholinyl, or —N(R2)C(O)NH(R3). In a preferred embodiment R1 is —C(O)N(R2)(R3). In a preferred embodiment, R1 is —SO$_2$N(R2)(R3), —SO$_2$—N-pyrrolidinyl (wherein the pyrrolidine is optionally substituted with R4), —SO$_2$—N-piperidinyl (wherein the piperidine is optionally substituted with R4), or —SO$_2$—N-morpholinyl.

In a preferred embodiment R1 is —X—(CH$_2$)$_n$—R5 (wherein X=—S— and n is 0, 1, 2, 3, or 4), wherein when n is 0 then (CH$_2$)$_n$ is a bond; provided however that wherein X is —S— and n is 0 or 1, then R5 is not —N(R2)(C$_1$-C$_6$) alkyl, —N(R2)(C$_3$-C$_7$cycloalkyl), —N(R2)(CH$_2$) phenyl, —N-pyrrolidinyl, —N-piperidinyl, —N-morpholinyl, or —N-piperazine-N-methyl. In a preferred embodiment R1 is —X—(CH$_2$)$_n$—R5 (wherein X=—CH$_2$— and n is 0, 1, 2, 3, or 4), wherein when n is 0 then (CH$_2$)$_n$ is a bond; provided however that wherein X is —S— and n is 0 or 1, then R5 is not —N(R2)(C$_1$-C$_6$) alkyl, —N(R2)((C$_3$-C$_7$)cycloalkyl), —N(R2)(CH$_2$) phenyl, —N-pyrrolidinyl, —N-piperidinyl, —N-morpholinyl, or —N-piperazine-N-methyl.

In a preferred embodiment R1 is independently
—N(H)—CH$_2$—CH$_2$—N-pyrrolidinyl; —N(H)—CH$_2$—CH$_2$—CH$_2$—N-piperidinyl; —N(H)—CH$_2$—CH$_2$—CH$_2$—CH$_3$; —N(—CH$_2$—CH$_3$)(—CH$_2$—CH$_3$); —N-piperidinyl;

—N(H)—C(O)—N(H)—CH$_2$—CH$_2$—CH$_2$—CH$_3$;
—SO$_2$—N(—CH$_2$CH$_3$)(—CH$_2$CH$_3$);

—N(—CH$_3$)(—CH$_3$); —CH$_2$—CH$_2$—N(H)(-cyclopentyl); —CH$_2$—CH$_2$—CH$_2$—N(H)(-cyclopentyl);

—CH$_2$—CH$_2$—N(H)(—CH$_2$-phenyl); —CH$_2$—CH$_2$—N-piperidinyl; —CH$_2$—CH$_2$—N-pyrrolidinyl;

—CH$_2$—CH$_2$—CH$_2$—N-pyrrolidinyl; —CH$_2$—CH$_2$(—N-piperazinyl-N-methyl);

—CH$_2$—CH$_2$—N(CH$_2$—CH$_3$)(—CH$_2$—CH$_3$); —C(O)N(H)(—CH$_2$—CH$_2$—CH$_2$(—N-pyrrolidinyl);

—SO$_2$—N-pyrrolidinyl; —SO$_2$—N-morpholinyl; —SO$_2$—N-pyrrolidinyl-3-SO$_2$CH$_3$;

—N(H)(—SO$_2$—CH$_2$-phenyl); —N(H)(—SO$_2$-phenyl-4-SO$_2$CH$_3$);

—N(—CH$_3$)(—SO$_2$-phenyl-4-SO$_2$CH$_3$); —S—CH$_2$—CH$_2$—CH$_2$-4-pyridinyl;

—S—CH$_2$—CH$_2$—CH$_2$-3-pyridinyl; —S-4-pyridinyl; —C(O)N(H)—CH$_2$—CH$_2$-3-pyridinyl;

—S-4-pyrimidinyl; and —S-3-pyridinyl.

Preferably R2 is —H. Preferably R2 is —(C$_1$-C$_3$) alkyl. Preferably R2 is methyl or ethyl. Preferably R3 is —(C$_1$-C$_6$) alkyl (optionally substituted with one to three halogens). Preferably R4 is —SO$_2$CH$_3$. Preferably X is —S—. Preferably n is 2 or 3. Preferably R6 is —H. Preferably R7 is —H. Preferably R6 is —H and R7 is —H. Preferably R6 and R7 are independently —H or —CH$_3$. Preferably R6 is —CH$_3$ and R7 is —H.

Further embodiments of the invention include the compounds of formulae X1 to X28, or a pharmaceutically acceptable salt thereof. A further embodiment of the invention are any novel intermediate preparations described herein which are useful for preparing the histamine H3 receptor antagonists or inverse agonists of formulae I, or X1 to X28.

TABLE 1

| Formula Number | Structure |
| --- | --- |
| X1 | 4-(2-(pyrrolidin-1-yl)ethylamino)phenyl)(2-(pyrrolidin-1-ylmethyl)pyrrolidin-1-yl)methanone |
| X2 | (4-(3-(piperidin-1-yl)propylamino)phenyl)(2-(pyrrolidin-1-ylmethyl)pyrrolidin-1-yl)methanone |
| X3 | (4-(butylamino)phenyl)(2-(pyrrolidin-1-ylmethyl)pyrrolidin-1-yl)methanone |
| X4 | (4-(diethylamino)phenyl)(2-(pyrrolidin-1-ylmethyl)pyrrolidin-1-yl)methanone |
| X5 | (4-(piperidin-1-yl)phenyl)(2-(pyrrolidin-1-ylmethyl)pyrrolidin-1-yl)methanone |
| X6 | 1-butyl-3-(4-(2-(pyrrolidin-1-ylmethyl)pyrrolidine-1-carbonyl)phenyl)urea |

TABLE 1-continued
| Formula Number | Structure |
|---|---|
| X7 | 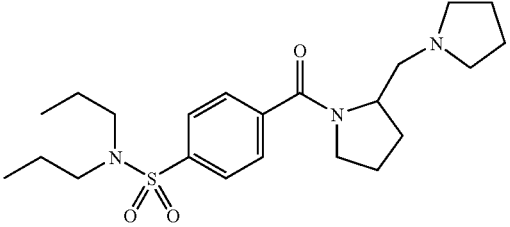 |
| X8 | 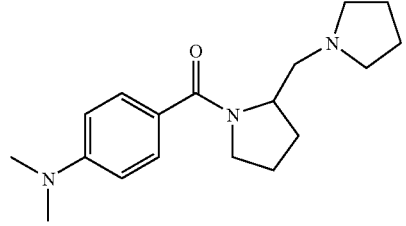 |
| X9 | 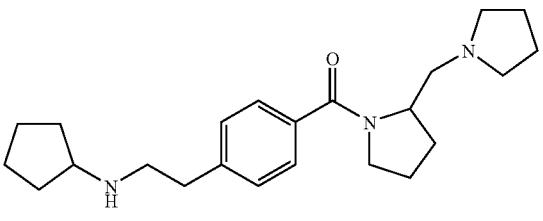 |
| X10 | 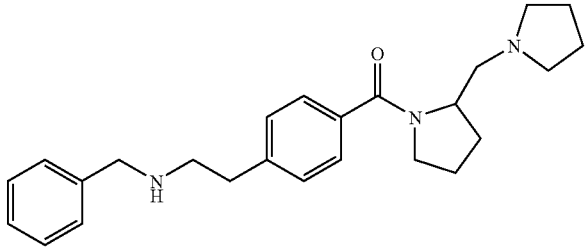 |
| X11 | 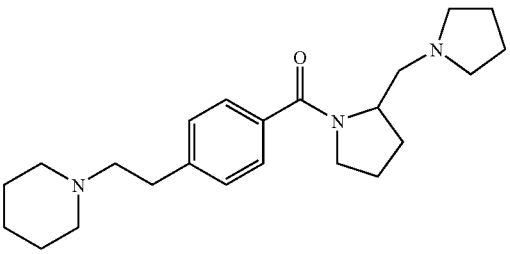 |
| X12 | 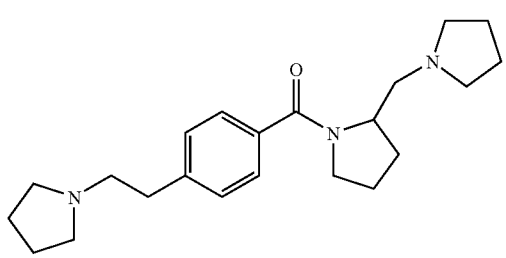 |

TABLE 1-continued
| Formula Number | Structure |
|---|---|
| X13 | 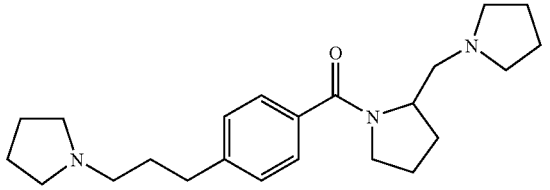 |
| X14 | 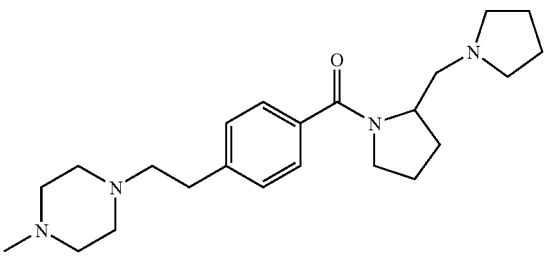 |
| X15 | 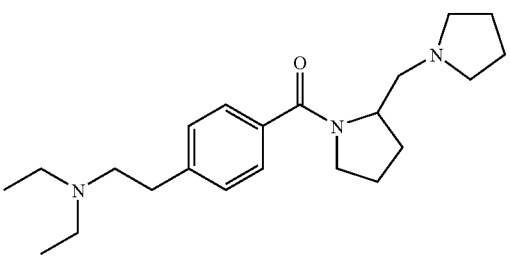 |
| X16 | 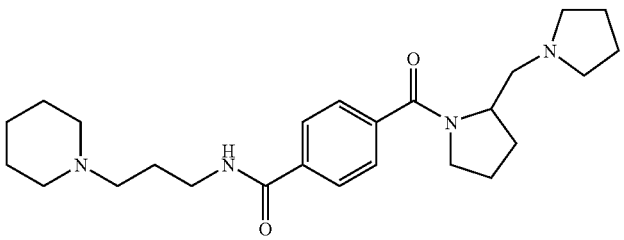 |
| X17 | 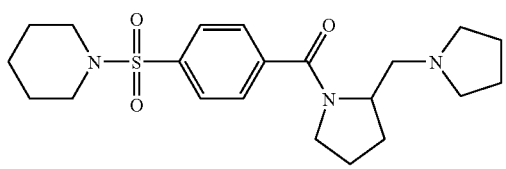 |
| X18 | 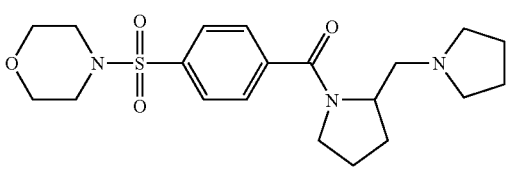 |
| X19 | 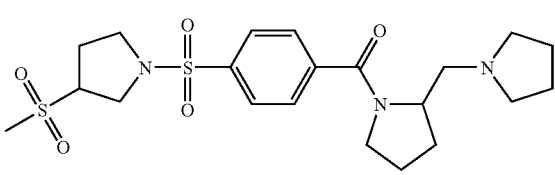 |

TABLE 1-continued

| Formula Number | Structure |
|---|---|
| X20 | 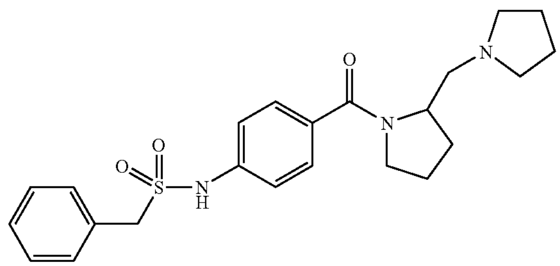 |
| X21 | 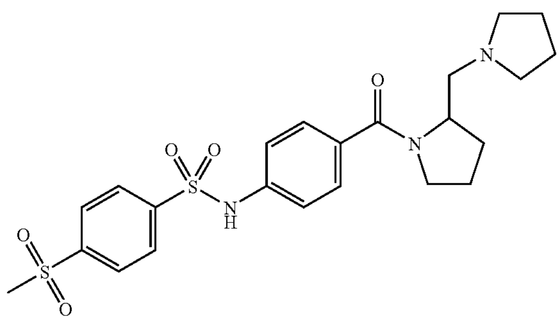 |
| X22 | 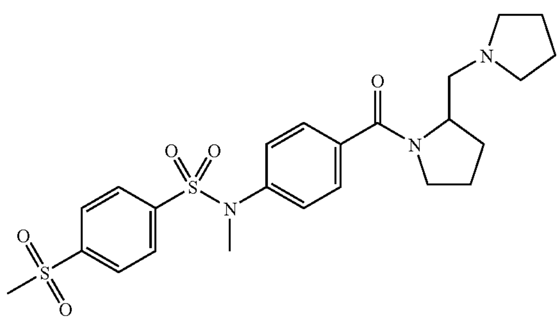 |
| X23 | 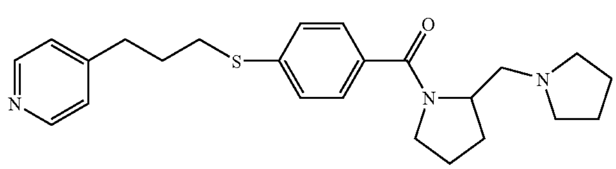 |
| X24 | 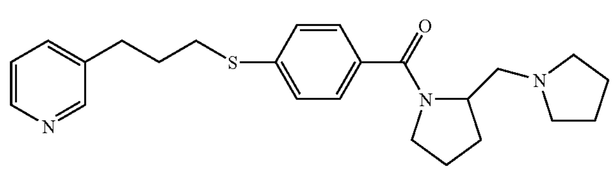 |
| X25 | 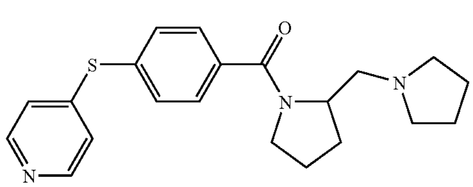 |

TABLE 1-continued

| Formula Number | Structure |
|---|---|
| X26 | [chemical structure] |
| X27 | [chemical structure] |
| X28 | [chemical structure] |

The present invention further provides an antagonist or inverse agonist of Formula I which is characterized by having little or no binding affinity for the histamine receptor GPRv53. Due to their interaction with the histamine H3 receptor, the present compounds are useful in the treatment of a wide range of conditions and disorders in which an interaction with the histamine H3 receptor is beneficial. Thus, the methods of this invention encompass a prophylactic and therapeutic administration of a compound or pharmaceutical composition of Formula I. The present invention also provides a pharmaceutical composition which comprises a compound of Formula I and a pharmaceutically acceptable carrier. Pharmaceutical formulations of Formula I can provide a method of selectively increasing histamine levels in cells, or increasing histamine release by cells, by contacting the cells with an antagonist or inverse agonist of the histamine H3 receptor, the antagonist or inverse agonist being a compound of Formula I.

Thus, the compounds or pharmaceutical compositions of formula I may find use for example to prevent, treat and/or alleviate diseases or conditions of the central nervous system, the peripheral nervous system, the cardiovascular system, the pulmonary system, the gastrointestinal system and the endocrinological system, while reducing and or eliminating one or more of the unwanted side effects associated with the current treatments.

In addition, the present invention provides to a compound of Formula I, or a pharmaceutical salt thereof, or a pharmaceutical composition which comprises a compound of Formula I, or a pharmaceutical salt thereof, and a pharmaceutically acceptable carrier, diluent, or excipient; for use in inhibiting the histamine H3 receptor; for use in inhibiting a histamine H3 receptor mediated cellular response in a mammal; for use to increase the release of H3 receptor-regulated neurotransmitters in a mammal; for use in treating a disease arising from excessive histamine H3 receptor activity; and for use in treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive deficits in psychiatric disorders, deficits of memory, deficits of learning, dementia, mild cognitive impairment, migraine, mood and attention alteration, motion sickness, neurogenic inflammation, obsessive compulsive disorder, Parkinson's disease, schizophrenia, depression, seizures or convulsions; sleep disorders such as narcolepsy; vestibular dysfunction such as Meniere's disease, pain, drug abuse, depression, epilepsy, jet lag, wakefulness, Tourette's syndrome, and vertigo.

The present invention is further related to the use of a compound of Formula I, or a pharmaceutical salt thereof, or a pharmaceutical composition which comprises a compound of Formula I, or a pharmaceutical salt thereof, and a pharmaceutically acceptable carrier, diluent, or excipient; for the manufacture of a medicament for inhibiting the histamine H3 receptor; for the manufacture of a medicament for inhibiting a histamine H3 receptor mediated cellular response in a mammal; for the manufacture of a medicament to increase the release of H3 receptor-regulated neurotransmitters in the brain of a mammal; for the manufacture of a medicament for treating a disease arising from excessive histamine H3 receptor activity; for the manufacture of a medicament for treating cognitive disorders in a mammal; and for the manufacture of a medicament for treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive deficits in psychiatric disorders, deficits of memory, deficits of learning, dementia, mild cognitive impairment, migraine, mood and attention alteration, motion sickness, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, pain, drug abuse, depression, jet lag, wakefulness, Tourette's syndrome, and vertigo. In another embodiment of the invention the present compounds are used for the preparation of a medicament for the treatment of any histamine H3 receptor -mediated conditions and diseases.

The present invention further provides; a method of treating conditions resulting from excessive histamine H3 receptor activity in a mammal; a method of inhibiting the histamine H3 receptor activity in a mammal; a method of inhibiting a histamine H3 receptor mediated cellular response in a mammal; a method to increase the release of H3 receptor-regulated neurotransmitters in the brain of a mammal; a method of treating cognitive disorders in a mammal; a method of treating nervous system disorders in a mammal including but not limited to obesity, cognitive disorders, attention and attention deficit disorders, memory processes, learning deficits, dementia, Alzheimer's disease, attention-deficit hyperactivity disorder, Parkinson's disease, schizophrenia, depression, epilepsy, and seizures or convulsions; said methods comprising administering to a mammal in need of such treatment a histamine H3 receptor-inhibiting amount of a compound of Formula I or a pharmaceutically acceptable salt thereof, or a pharmaceutical composition which comprises a compound of Formula I, or a pharmaceutical salt thereof, and a pharmaceutically acceptable carrier, diluent, or excipient.

The present invention further provides a method of treating conditions resulting from excessive histamine H3 receptor activity in a mammal comprising administering to a mammal in need of such treatment a histamine H3 receptor inhibiting amount of a pharmaceutical composition which comprises a compound of Formula I, or a pharmaceutical salt thereof, and a pharmaceutically acceptable carrier, diluent, or excipient. In addition, a pharmaceutical composition of Formula I can be useful in the treatment or prevention of a disorder or disease in which modulation of histamine H3 receptor activity has a beneficial effect. The present invention further provides an antagonist or inverse agonist of Formula I which is characterized by having greater affinity for the histamine H3 receptor as compared to the affinity for the histamine H1R, H2R, or H4R receptors. In still another embodiment of the invention the present compounds are used for the preparation of a pharmaceutical composition for the treatment of an appetite regulation or energy expenditure disorder. In a further embodiment of the invention, treatment of a patient with the present compounds is combined with diet and/or exercise. In another embodiment the intermediate compounds are useful for preparing final compounds of the invention. In addition the embodiments of the present invention include the synthesis of the examples named herein by methods included herein, and supplemented by methods known in the art, to create positron emission topography (PET) ligands that bind to histamine H3 receptors and are useful for PET imaging.

The invention includes tautomers, enantiomers and other stereoisomers of the compounds also. Thus, as one skilled in the art knows, certain aryls may exist in tautomeric forms. Such variations are contemplated to be within the scope of the invention. It will be understood that, as used herein, references to the compounds of Formula I are meant to also include the pharmaceutical salts, enantiomers and racemic mixtures thereof. The compounds of the present invention may be chiral, and it is intended that any enantiomers, as separated, pure or partially purified enantiomers or racemic mixtures thereof are included within the scope of the invention.

The designation " ⟶ " refers to a bond that protrudes forward out of the plane of the page. The designation " ⦀ " refers to a bond that protrudes backward out of the plane of the page. The designation " ∿ " refers to a bond wherein the stereochemistry is not defined.

The compounds of Formula I, when existing as a diastereomeric mixture, may be separated into diastereomeric pairs of enantiomers by, for example, fractional crystallization from a suitable solvent, such as methanol or ethyl acetate, or a mixture thereof. The pair of enantiomers thus obtained may be separated into individual stereoisomers by conventional means, for example by the use of an optically active acid as a resolving agent. Alternatively, any enantiomer of a compound of Formula I may be obtained by stereospecific synthesis using optically pure starting materials or reagents of known configuration or through enantioselective synthesis.

The stereoisomers and enantiomers of compounds of Formula I can be prepared by one of ordinary skill in the art utilizing well known techniques and processes, such as those disclosed by J. Jacques, et al., "*Enantiomers, Racemates, and Resolutions,*" John Wiley and Sons, Inc., 1981, and E. L. Eliel and S. H. Wilen, "*Stereochemistry of Organic Compounds,*" (Wiley-Interscience 1994), and European Patent Application No. EP-A-838448, published Apr. 29, 1998.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into a compound of the present invention. Conventional procedures for the selection and preparation of suitable prodrug derivatives are described, for example in "Design of Prodrugs", ed. H. Bundgaard, Elsevier, 1985.

The compounds of Formula I can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Procedures, Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example, as used herein, the following terms have the meanings indicated; "min" refers to minutes; "h" or "hr" refers to hours; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry; "MS (ES)" refers to electron spray mass spectrometry; "APCI" refers to atmospheric chemical ionization; "UV" refers to ultraviolet spectrometry; "$^1$H NMR" refers to proton nuclear magnetic resonance spectrometry; "RT" refers to room temperature; "PS-Trisamine" is Tris-(2-aminoethyl)amine polystyrene; "PS-Carbodiimide" or "PS-CDI" refers to N-Cyclohexylcarbodiimide-N'-propyloxymethyl polystyrene; "PS-DIEA" refers to N,N-(Diisopropyl)aminomethylpolystyrene (1% inorganic antistatic agent); "PS-DMAP" refers to N-(methylpolystyrene)-4-(methylamino) pyridine; "Boc" or "BOC" refer to t-butyl carbamate; "HOBt" is 1-hydrobenzotriazole; "MeOH" refers to methanol; "DMF" refers to dimethylformamide; "EtOAc" refers to ethyl acetate.

General Schemes

SCHEME A

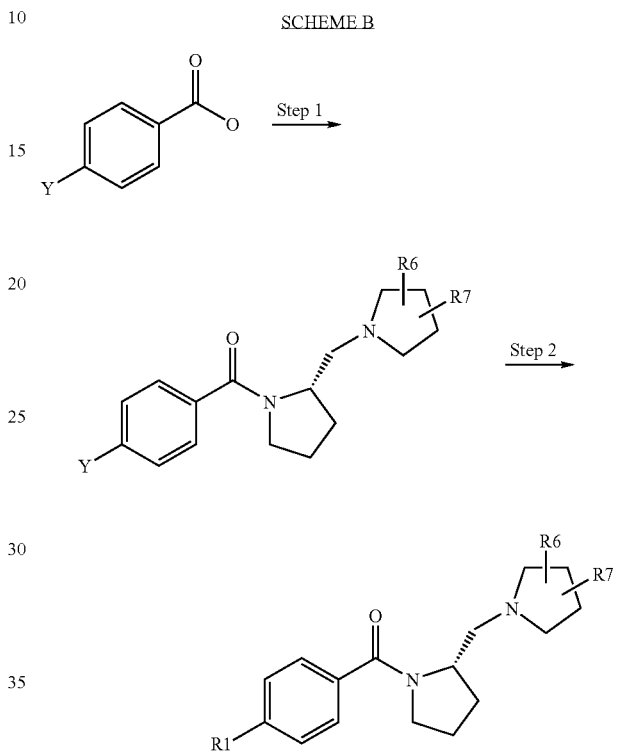

In Scheme A, $R_a$ is H, or the corresponding acid salts. In Scheme 1, Step 1 the carboxylic acids or the lithium, sodium or potassium salt of the acid where $R_a$ can be H, Li, Na or K are converted to the corresponding amides using a number of different coupling methods known in the literature. Some of these methods are described in Klausner & Bodansky, Synthesis, 1972, 9, 453-463.

For example, 4-(piperidine-1-sulfonyl)-benzoic acid (where R1=4-(piperidine-1-sulfonyl) or the corresponding lithium or sodium salt is suspended a suitable organic solvent such as dichloromethane, DMF or mixtures thereof. A suitable amide coupling agent i.e. TBTU, or HATU, is added, or EDC, DCC, etc., is added, followed by HOBt, etc., at room temperature. An amine base, such as diisopropylethyl amine and suitable amine in this case, (S)(+)-1-(2-pyrrolidinylmethyl)pyrrolidine are added to the mixture. The mixture is stirred at room temperature for a period of 8-48 hours. The reaction is quenched by addition of water. The resulting mixture may be extracted, concentrated and purified according to techniques well known in the art.

Alternatively the corresponding acid chloride can be formed from the corresponding acid or salt thereof using thionyl chloride or oxalyl chloride and a few drops of DMF, and treated with a suitable amine to give the desired amide.

For example, 1.00 g of 4-(2-chloroethyl)benzoic acid (where R1=4-(2-chloroethyl)) is dissolved in 10 ml of thionyl chloride and stirred under reflux for a period of 1-12 hours and excess thionyl chloride is removed in vacuo. The residue is dissolved in a suitable solvent in this case $CH_2Cl_2$ to make an acid chloride solution and is added to a solution of a suitable amine in this case (S)(+)-1-(2-pyrrolidinylmethyl) pyrrolidine and a proton scavenger i.e. triethylamine in $CH_2Cl_2$. The mixture is stirred at room temperature for a period of 30 minutes to 12 hours. The resulting mixture may be concentrated, extracted, and purified according to techniques well known in the art.

SCHEME B

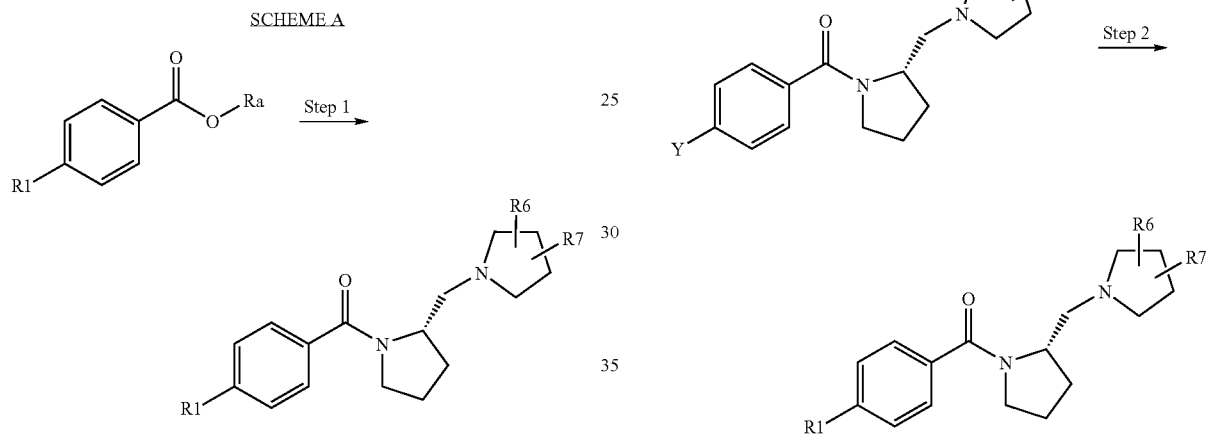

In Scheme B, Y is any group that contains a functional group that can be further modified to R1 via alkylation, acylation, oxidation, reduction, sulfonylation, displacement, etc. In Scheme B, Step 1, the carboxylic acids are converted to the pyrrolidinylmethylpyrrolidine amides by the methods described in Scheme A (step 1).

For example, (4-fluoro-phenyl)-(2-pyrrolidin-1-ylmethyl-pyrrolidin-1-yl)-methanone (where Y=F) is treated with a suitable nucleophile, in this case, 2-pyrrolidin-1-yl-ethylamine in a suitable solvent such as DMSO and 33% $KF/Al_2O_3$ and the reaction is heated for 1-3 days to yield [4-(2-pyrrolidin-1-yl-ethylamino)-phenyl]-(2-pyrrolidin-1-ylmethyl-pyrrolidin-1-yl)-methanone.

For example, 4-(2-chloro-ethyl)-phenyl]-(2-pyrrolidin-1-ylmethyl-pyrrolidin-1-yl)-methanone (where Y=2-chloroethyl) is treated with a suitable nucleophile, in this case, cyclopentylamine in a suitable solvent such as DMF and with NaI and the reaction is heated for 1-3 days to yield [4-(2-cyclopentylamino-ethyl)-phenyl]-(2-pyrrolidin-1-ylmethyl-pyrrolidin-1-yl)-methanone.

For example, (4-bromo-phenyl)-(2-pyrrolidin-1-ylmethyl-pyrrolidin-yl)methanone (where Y=Br) is treated with a suitable nucleophile, in this case, 4-mercaptopyridine in a suitable solvent such as DMF with potassium carbonate and the reaction heated to reflux for 1-3 days to yield [4-(pyridin-4-ylsulfanyl)-phenyl]-(2-pyrrolidin-1-ylmethyl-pyrrolidin-1-yl)-methanone.

SCHEME C

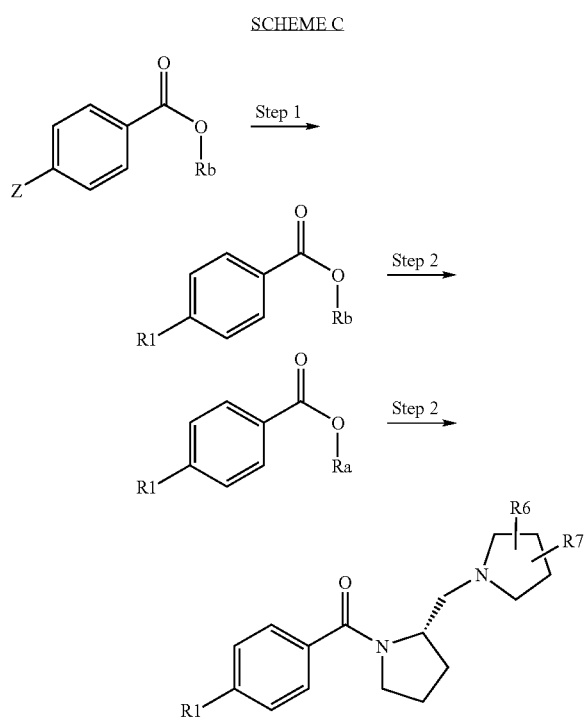

Alternatively, wherein Z=SH, the thiol group can be converted to R1 by alkylation with an alkyl halide or methane sulfonyl alkyl ester. For example, 4-mercapto-benzoic acid methyl ester is treated with an alkylating agent, in this case methanesulfonic acid 3-pyridin-4-yl-propyl ester (prepared by sulfonylation of the alcohol) in a suitable solvent such as DMF in the presence of potassium carbonate and heated for 2-24 hours to yield 4-(3-pyridin-4-yl-propylsulfanyl)-benzoic acid methyl ester.

In Scheme C, Step 2, the resulting esters (wherein $R_b$=Me, Et, Bz etc.), can be saponified using standard conditions to yield the corresponding carboxylic acids or the lithium, sodium or potassium salt of the acid where $R_a$ can be H, Li, Na or K. For example, 3-(1-methanesulfonyl-piperidin-4-ylmethyl)-benzoic acid methyl ester is dissolved in a suitable solvent such as MeOH or dioxane and 1M LiOH is added. The reaction mixture is stirred at room temperature overnight or can be heated to 50° C. for 30 minutes to 18 hours. The solvent is removed in vacuo and the acid or salt isolated according to techniques well known in the art.

In Scheme C, Step 3, the carboxylic acids or the corresponding lithium, sodium or potassium salts (wherein $R_a$=H, Li, Na, K) are converted to the pyrrolidinylmethylpyrrolidine amides by the methods described in Scheme A, Step 1.

SCHEME D

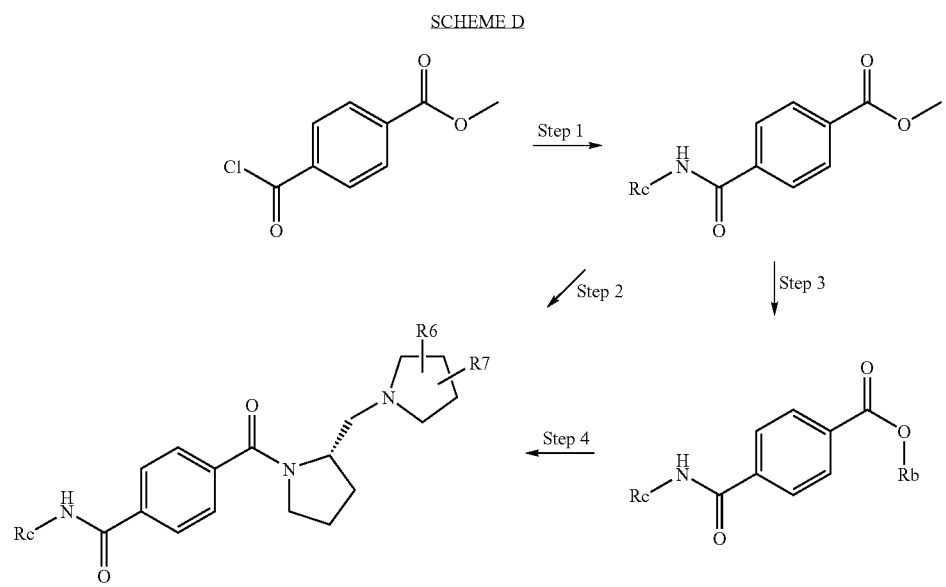

In Scheme C, Z=NH₂ or SH and Rb can be but is not limited to the corresponding methyl, ethyl, or benzyl esters. In Scheme C, Step 1 (wherein Z=NH₂) the amino group can be converted to R1 by acylation, sulfonylation, alkylation, or displacement.

For example, 4-amino-benzoic acid methyl ester, is treated with a sulfonyl halide, in this case 4-methanesulfonyl benzenesulfonyl chloride, in a suitable solvent, such as a 1:1 mixture of dichloromethane and pyridine at ambient temperature for 2-24 hours to yield 4-(4-methanesulfonyl-benzenesulfonylamino)-benzoic acid methyl ester.

In Scheme D, $R_c$ is an alkyl group such that C(O)NHR$_c$=R1. In Scheme D, Step 1, the acid chloride is acylated with an alkyl group to give an amide.

For example, terephtalic acid monomethyl ester chloride is treated with an alkylamine, in this case 3-piperidinopropylamine, and triethylamine, in a suitable solvent such as dichloromethane at ambient temperature for 1-12 hours to provide the desired amide, N-(3-piperidin-1-yl-propyl)-terephthalamic acid methyl ester.

In Scheme D, Step 2, the methyl ester is converted directly to the pyrrolidine amide by treatment with 1-(2-pyrrolodinylmethyl)pyrrolidine and trimethyl aluminum in a suitable solvent such as tetrahydrofuran. The mixture is stirred at ambient temperature for 2-24 hours to provide N-(3-piperidin-1-yl-propyl)-4-(2-(S)-pyrrolidin-1-ylmethyl-pyrrolidine-1-carbonyl)-benzamine.

Alternatively, in Scheme D, Step 3, the methyl ester can be saponified to the corresponding carboxylic acids or the lithium, sodium, or potassium salt of the acid (wherein $R_b$=H, Li, Na, or K) as described in Scheme C (Step 2).

In Scheme D, Step 3, the carboxylic acids or the corresponding lithium, sodium or potassium salts (wherein $R_b$=H, Li, Na, K) are converted to the pyrrolidinylmethylpyrrolidine amides by the methods described in Scheme A, Step 1.

PREPARATIONS AND EXAMPLES

Intermediate 1

(4-Fluoro-phenyl)-(2-(S)-pyrrolidin-1-ylmethyl-pyrrolidin-1-yl)-methanone (S)(+)-1-(2-Pyrrolidinylmethyl)pyrrolidine (1.07 g, 6.93 mmol) and triethylamine (763 mg, 7.56 mmol) are dissolved in dichloromethane (20 mL) and cooled to 0° C. 4-Fluorobenzoyl chloride (1.00 g, 6.3 mmol) in dichloromethane (2 mL) is added to the mixture at 0° C. and stirred at room temperature for 3 h. The reaction mixture is washed with brine, dried over $Na_2SO_4$, and evaporated. The residue is purified by silica-gel column chromatography ($CH_2Cl_2$:2M $NH_3$ in MeOH=40:1) to give 1.45 g (83%) of the title compound. MS (APCI+) 277(M+1)$^+$.

Example 1

[4-(2-Pyrrolidin-1-yl-ethylamino)-phenyl]-(2-(S)-pyrrolidin-1-ylmethyl-pyrrolidin-1-yl)-methanone

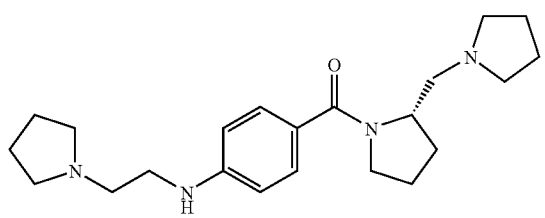

Procedure A (4-Fluoro-phenyl)-(2-(S)-pyrrolidin-1-ylmethyl-pyrrolidin-1-yl)-methanone (352 mg, 1.27 mmol) and 2-pyrrolidin-1-yl-ethylamine (913 mg, 8.0 mmol) are combined in a 4.0 ml vial with DMSO (2 mL), followed by addition of 33% $KF/Al_2O_3$(320 mg). The vial is heated at 160° C. for 3 days. The reaction mixture is filtered and the filtrate is diluted with $CH_2Cl_2$, washed with brine, dried over $Na_2SO_4$, and evaporated. The crude material is purified by silica-gel chromatography ($CH_2Cl_2$:2M $NH_3$ in MeOH=20:1) to give 69 mg (15%) of the title compound. MS (APCI+) 371 (M+1)$^+$.

Example 2

[4-(3-Piperidin-1-yl-propylamino)-phenyl]-(2-(S)-pyrrolidin-1-ylmethyl-pyrrolidin-1-yl)-methanone

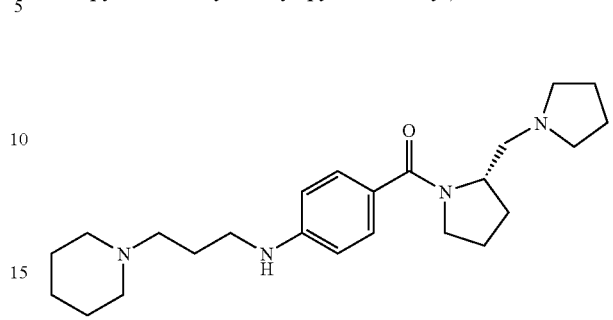

(S)-[4-(3-Diethylamino-propylamino)-phenyl]-(2-pyrrolidin-1-ylmethyl-pyrrolidin-1-yl)-methanone is prepared from (4-Fluoro-phenyl)-(2-pyrrolidin-1-ylmethyl-pyrrolidin-1-yl)-methanone and 3-piperidino propylamine in a manner substantially similar to Procedure A. MS (APCI+) 399 (M+H)$^+$.

Example 3

(4-Butylamino-phenyl)-(2-(S)-pyrrolidin-1-ylmethyl-pyrrolidin-1-yl)-methanone

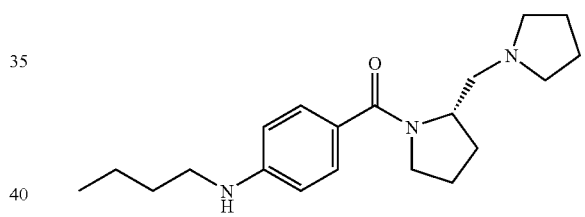

(4-Butylamino-phenyl)-(2-(S)-pyrrolidin-1-ylmethyl-pyrrolidin-1-yl)-methanone is prepared from (4-Fluoro-phenyl)-(2-(S)-pyrrolidin-1-ylmethyl-pyrrolidin-1-yl)-methanone and n-butylamine in a manner substantially similar to Procedure A. MS (APCI+) 330 (MA-H)$^+$.

Example 4

(4-Diethylamino-phenyl)-(2-(S)-pyrrolidin-1-ylmethyl-pyrrolidin-1-yl)-methanone

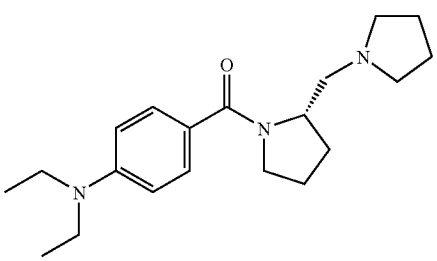

(4-Diethylamino-phenyl)-(2-(S)-pyrrolidin-1-ylmethyl-pyrrolidin-1-yl)-methanone is prepared from (4-Fluoro-phenyl)-(2-pyrrolidin-1-ylmethyl-pyrrolidin-1-yl)-methanone and diethylamine in a manner substantially similar to Procedure A. MS (APCI+) 330 (M+H)⁺.

Example 5

(4-Piperidin-1-yl-phenyl)-(2-(S)-pyrrolidin-1-ylmethyl-pyrrolidin-1-yl)-methanone

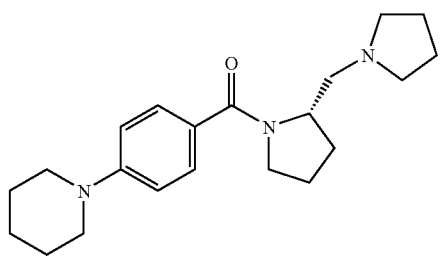

Procedure B

4-Piperidin-1-yl benzoic acid (96 mg, 0.47 mmol), (S)(+)-1-(2-pyrrolidinylmethyl)pyrrolidine (86 mg, 0.56 mmol), and PS-carbodiimide (424 mg, 0.56 mmol) are placed into the reaction vial with 5% DMF in dichloromethane (5 mL) and mixed well. The reaction vial is sealed with a Teflon cap and shaken at room temperature for 3 days. The reaction mixture is filtered and washed with dichloromethane. The filtrate is concentrated and the resulting residue purified by silica-gel column chromatography (CH$_2$Cl$_2$:2M NH$_3$ in MeOH=45:1) to give 50 mg (31%) of the title compound. MS (APCI+) 342 (M+H)⁺.

Example 6

1-Butyl-3-[4-(2-(S)-pyrrolidin-1-ylmethyl-pyrrolidine-1-carbonyl)-phenyl]-urea

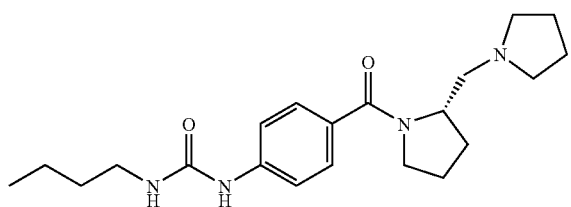

The title compound is prepared from 4-(3-butyl ureido) benzoic acid (CAS 51739-79-8) in a manner substantially similar to Procedure B. MS (APCI+) 373 (M+H)⁺.

Example 7

N,N-Dipropyl-4-(S)-pyrrolidin-1-ylmethyl-pyrrolidine-1-carbonyl)-benzenesulfonamide

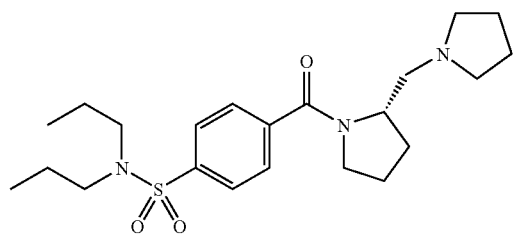

The title compound is prepared from 4-dipropyl sulfanyl benzoic acid in a manner substantially similar to Procedure B. MS (APCI+) 422 (M+H)⁺.

Example 8

(4-Dimethylamino-phenyl)-(2-(S)-pyrrolidin-1-ylmethyl-pyrrolidin-1-yl)-methanone

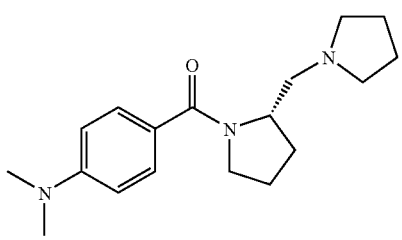

The title compound is prepared from 4-methylaminobenzoic acid in a manner substantially similar to Procedure B. MS (APCI+) 302 (M+H)⁺.

Intermediate 2

[4-(2-Chloro-ethyl)-phenyl]-(2-(S)-pyrrolidin-1-ylmethyl-pyrrolidin-1-yl)-methanone Procedure C 4-(2-Chloroethyl)benzoic acid (1.00 g, 5.4 mmol) is dissolved in thionyl chloride (6.0 mL) and stirred at 50° C. for 30 min. The excess thionyl chloride is removed in vacuo and the residue is dissolved in dichloromethane (2 mL) to make a solution of the acid chloride. Triethylamine (656 mg, 6.5 mmol) and (S)(+)-1-(2-pyrrolidinylmethyl)pyrrolidine (1.00 g, 6.5 mmol) are dissolved in dichloromethane (30 mL) and cooled to 0° C. The acid chloride solution is added to this mixture at 0° C. and stirred at room temperature for 2 h. The reaction mixture is diluted with CH$_2$Cl$_2$, washed with brine, dried over Na$_2$SO$_4$, and evaporated. The crude product is purified by silica-gel column chromatography (CH$_2$Cl$_2$:2M NH$_3$ in MeOH=40:1) to give 1.35 g (80%) of the title compound. MS (APCI+) 321 (M+H)⁺.

Example 9

[4-(2-Cyclopentylamino-ethyl)-phenyl]-(2-(S)-pyrrolidin-1-ylmethyl-pyrrolidin-1-yl)-methanone

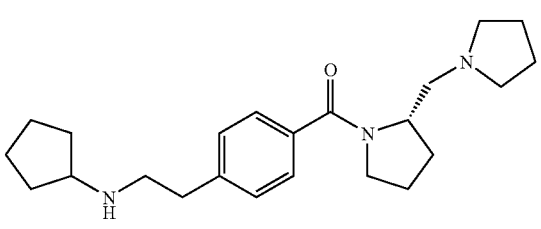

Procedure D

[4-(2-Chloro-ethyl)-phenyl]-(2-(S)-pyrrolidin-1-ylm-ethyl-pyrrolidin-1-yl)-methanone (190 mg, 0.59 mmol) and cyclopentylamine (151 mg, 1.77 mmol) are combined in a 4.0 ml vial with 5% DMF in tetrahydrofuran (2 mL), followed by addition of sodium iodide (10 mg). The vial is sealed with a Teflon cap and heated at 100° C. for 3 days and then allowed to cool to room temperature. The reaction mixture is concentrated under nitrogen gas and purified by silica-gel column chromatography (CH$_2$Cl$_2$:2M NH$_3$ in MeOH=20:1) to give 46 mg (22%) of the title compound. MS (APCI+) 370 (M+H)+.

Example 10

[4-(2-Cyclopentylamino-ethyl)-phenyl]-(2-(S)-pyrrolidin-1-ylmethyl-pyrrolidin-1-yl)-methanone dihydrochloride

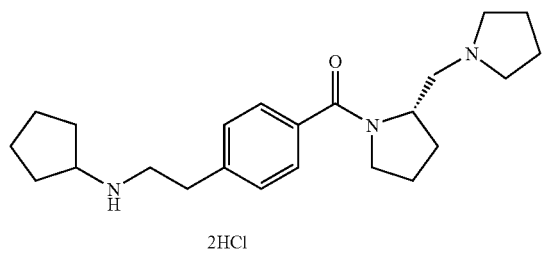

2HCl

[4-(2-Cyclopentylamino-ethyl)-phenyl]-(2-(S)-pyrrolidin-1-ylmethyl-pyrrolidin-1-yl)-methanone (100 mg) is dissolved in ether and 1 equivalent of 1M HCl in ether is added dropwise. The resulting precipitate is filtered and dried under vacuum to yield the dihydrochloride salt (95 mg, 79%). MS (ES+) 370.2 (M+H)+.

Example 11

[4-(2-Benzylamino-ethyl)-phenyl]-(2-(S)-pyrrolidin-1-ylmethyl-pyrrolidin-1-yl)-methanone

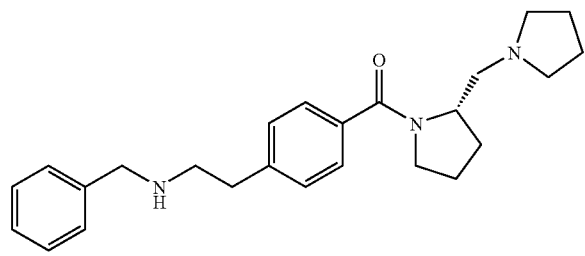

Example 12 is prepared from Intermediate 2 and benzylamine in a manner substantially similar to Procedure D. MS (APCI+) 392 (M+H)+.

Example 12

[4-(2-Piperidin-1-yl-ethyl)-phenyl]-(2-(S)-pyrrolidin-1-ylmethyl-pyrrolidin-1-yl)-methanone

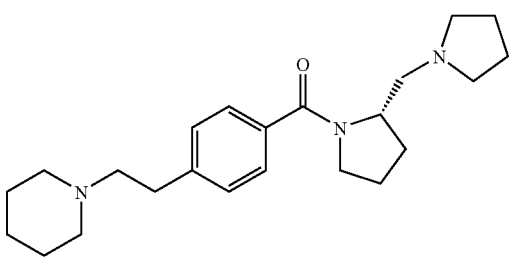

Example 12 is prepared from Intermediate 2 and piperidine in a manner substantially similar to Procedure D. MS (APCI+) 370 (M+H)+.

Example 13

[4-(2-Pyrrolidin-1-yl-ethyl)-phenyl]-(2-(S)-pyrrolidin-1-ylmethyl-pyrrolidin-1-yl)-methanone

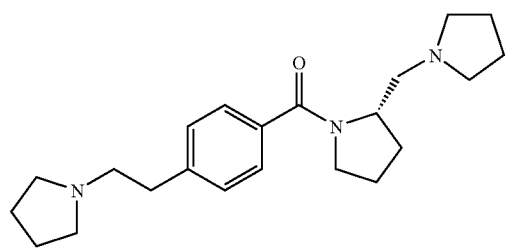

Example 13 is prepared from Intermediate 2 and pyrrolidine in a manner substantially similar to Procedure D. MS (APCI+) 356 (M+H)+.

Example 14

(S)-(2-Pyrrolidin-1-ylmethyl-pyrrolidin-1-yl)-[4-(3-pyrrolidin-1-yl-propyl)-phenyl]-methanone

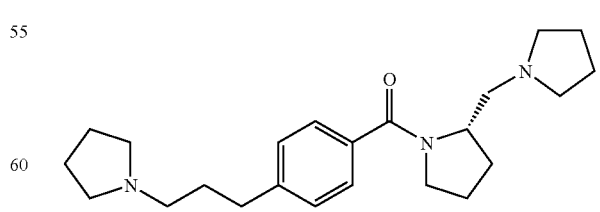

Example 14 is prepared from 4-(3-bromo-propyl)-benzoic acid (CAS 6309-79; Schmid, C. R., et. al. *Bioorg. Med. Chem. Lett.* 9 (1999) 523) in a manner substantially similar to Procedure B and D. MS (APCI+) 370 (M+H)+.

Example 15

{4-[2-(4-Methyl-piperazin-1-yl)-ethyl]-phenyl}-(2-(S)-pyrrolidin-1-ylmethyl-pyrrolidin-1-yl)-methanone

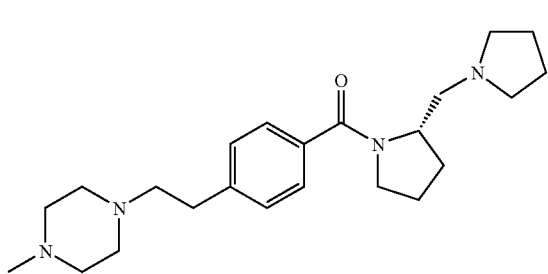

Example 15 is prepared from Intermediate 2 and 1-methylpiperazine in a manner substantially similar to Procedure D. MS (APCI+) 385 (M+H)$^+$.

Example 16

[4-(2-Diethylamino-ethyl)-phenyl]-(2-(S)-pyrrolidin-1-ylmethyl-pyrrolidin-1-yl)-methanone

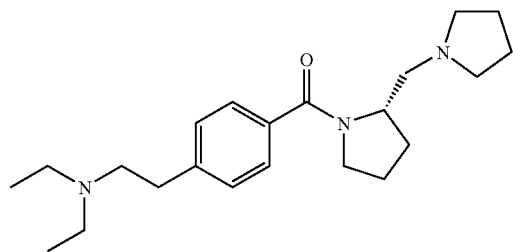

Example 16 is prepared from Intermediate 2 and diethylamine in a manner substantially similar to Procedure D. MS (APCI+) 358 (M+H)$^+$.

Intermediate 3

N-(3-Piperidin-1-yl-propyl)-terephthalamic acid methyl ester

Triethylamine (250 mg, 2.5 mmol) and 3-piperidinopropylamine (284 mg, 2.0 mmol) are dissolved in CH$_2$Cl$_2$ (5 mL). Terephtalic acid monomethyl ester chloride (197 mg, 2.0 mmol) in 2.0 ml of CH$_2$Cl$_2$ is added to the mixture. The reaction mixture is stirred at room temperature for 2 h. The reaction is diluted with CH$_2$Cl$_2$ and washed with brine. The separated organic layer is dried over Na$_2$SO$_4$ and evaporated. The crude material is purified by silica-gel column chromatography (CH$_2$Cl$_2$:2M NH$_3$ in MeOH) to give 473 mg (78%) of the title compound. MS (APCI+) 305 (M+H)$^+$.

Example 17

N-(3-Piperidin-1-yl-propyl)-4-(2-(S)-pyrrolidin-1-ylmethyl-pyrrolidine-1-carbonyl)-benzamine

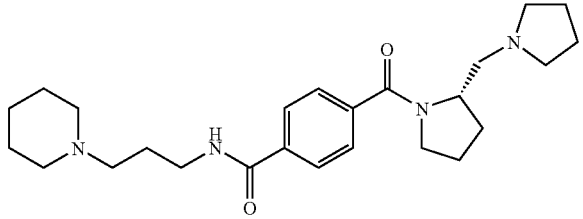

Procedure E (S)(+)-1-(2-Pyrrolidinylmethyl)pyrrolidine (287 mg, 1.86 mmol) is dissolved in dry tetrahydrofuran (2 mL) and trimethylaluminium (0.92 mL, 2.0M solution in toluene) is added. The mixture is stirred at room temperature for 1 h. N-(3-piperidin-1-yl-propyl)-terephthalamic acid methyl ester (470 mg, 1.54 mmol) is dissolved in tetrahydrofuran (2 mL) and the solution is added to the reaction mixture and stirred at room temperature overnight. The reaction mixture is diluted with CH$_2$Cl$_2$ and washed with brine. The separated organic layer is dried over Na$_2$SO$_4$ and evaporated. The crude material is purified by silica-gel column chromatography (CH$_2$Cl$_2$:2M NH$_3$ in MeOH=10:1) to give 490 mg (74%) of the title compound. MS (APCI+) 427 (M+H)$^+$.

Intermediate 4

4-(Piperidine-1-sulfonyl)-benzoic acid

Procedure F 4-(Chlorosulfonyl)benzoic acid (CAS 10130-89-9) (441 mg, 2.0 mmol) and triethylamine (202 mg, 2.0 mmol) are dissolved in dichloromethane (20 mL) and stirred under nitrogen while piperidine (340 mg, 4.0 mmol) in dichloromethane (5 mL) is added to the mixture at room temperature. After 18 h the reaction mixture is concentrated. The crude material is slurried in aqueous NaHCO$_3$, washed with diethyl ether, and separated. Ethyl acetate is added to the aqueous layer and the pH adjusted to 2 with 1N HCl. The layers are separated and the aqueous layer is extracted with EtOAc (2×). The EtOAc extracts are combined, washed with brine, dried over Na$_2$SO$_4$ and evaporated. The residue is purified by silica-gel column chromatography (0-8% MeOH/CH$_2$Cl$_2$ gradient) to give 350 mg (65%) of the title compound. MS (ES+) 270.1 (M+H)$^+$.

Example 18

[4-(Piperidine-1-sulfonyl)-phenyl]-(2-(S)-pyrrolidin-1-ylmethyl-pyrrolidin-1-yl)-methanone

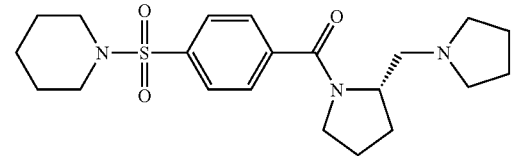

Procedure G 4-(Piperidine-1-sulfonyl)-benzoic acid (323 mg, 1.2 mmol) is stirred in 10% DMF/$CH_2Cl_2$ as 1-(3-dimethylaminopropyl)-3-carbodiimide hydrochloride (EDCI) (287 mg, 1.5 mmol) is added portionwise. Hydroxybenzotriazole (203 mg, 1.5 mmol) is added and the reaction is stirred at room temperature for 30-40 min. N,N-Diisopropylethylamine (0.47 mL, 2.7 mmol)) and (S)(+)-1-(2-pyrrolidinylmethyl)pyrrolidine (CAS 51207-66-0)(154 mg, 1.0 mmol) are added and the reaction is stirred 18 h. The reaction is diluted with $CH_2Cl_2$, washed with aqueous $NaHCO_3$ and brine, dried ($Na_2SO_4$), and concentrated in vacuo. The crude mixture is purified by SCX chromatography (MeOH wash, then elution with 2M $NH_3$/MeOH) and silica gel column chromatography (gradient: 100% $CH_2Cl_2$ to 10% 2M $NH_3$ in MeOH/$CH_2Cl_2$) to give 250 mg (61%) of the title compound. (MS (ES+) 406.2 $(M+H)^+$.

Intermediate 5

4-(Morpholine-4-sulfonyl)-benzoic acid

The title intermediate is prepared from 4-(chlorosulfonyl)benzoic acid (CAS 10130-89-9) (662 mg, 3.0 mmol) and morpholine (522 mg, 6.0 mmol) in a manner substantially similar to Procedure F to provide 450 mg (55%) of the title compound. MS (ES+) 272.3 $(M+H)^+$.

Example 19

[4-(Morpholine-4-sulfonyl)-phenyl]-(2-(S)-pyrrolidin-1-ylmethyl-pyrrolidin-1-yl)-methanone

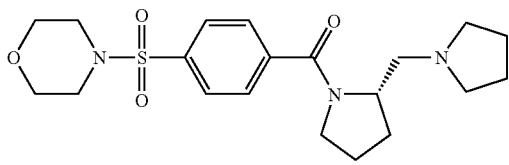

The title compound is prepared from 4-(morpholine-4-sulfonyl)-benzoic acid (407 mg, 1.5 mmol) and (S)(+)-1-(2-pyrrolidinylmethyl)pyrrolidine (CAS 51207-66-0)(193 mg, 1.2 mmol) in a manner substantially similar to Procedure G to provide 175 mg (34%) of the title compound. MS (ES+) 408.3 $(M+H)^+$.

Intermediate 6

4-(3-Methanesulfonyl-pyrrolidine-1-sulfonyl)-benzoic acid

The title intermediate is prepared from 4-(chlorosulfonyl)benzoic acid (CAS 10130-89-9) (375 mg, 1.7 mmol) and 3-(methylsulfonyl)pyrrolidine (CAS 433980-62-2) (343 mg, 2.3 mmol) in a manner substantially similar to Procedure F to provide 250 mg (44%) of the title compound. MS (ES−) 332.0 $(M-H)^-$.

Example 20

[4-(3-Methanesulfonyl-pyrrolidine-1-sulfonyl)-phenyl]-(2-(S)-pyrrolidin-1-ylmethyl-pyrrolidin-1-yl)-methanone

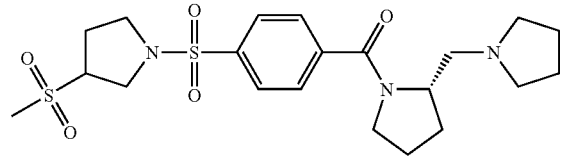

The title compound is prepared from 4-(3-methanesulfonyl-pyrrolidine-1-sulfonyl)-benzoic acid (230 mg, 0.69 mmol) and (S)(+)-1-(2-pyrrolidinylmethyl)pyrrolidine (CAS 51207-66-0)(88 mg, 0.57 mmol) in a manner substantially similar to Procedure G to provide 133 mg (50%) of the title compound. MS (ES+) 470.2 $(M+H)^+$.

Intermediate 7

4-(4-Methanesulfonyl-benzenesulfonylamino)-benzoic acid methyl ester

To a stirring solution of 4-amino-benzoic acid methyl ester (0.594 g, 3.93 mmol) in a mixture of dichloromethane (15 mL)/pyridine (15 mL) is added 4-methanesulfonyl benzenesulfonyl chloride (1.0 g, 3.93 mmol) and the mixture is allowed to react for 6 h at ambient temperature. The reaction is diluted with ethyl acetate and washed with 1N HCl. The organic layer is separated and dried over sodium sulfate, filtered, and concentrated to give 1.26 g (87%) of the title compound. MS (ES−) (m/e) 368.0 $(M-1)^-$.

Intermediate 8

4-(4-Methanesulfonyl-benzenesulfonylamino)-benzoic acid

To a stirring solution of 4-(4-methanesulfonyl-benzenesulfonylamino)-benzoic acid methyl ester (0.456 g, 1.26 mmol) in a mixture of tetrahydrofuran (10 mL)/methanol (10 mL) is added 2N sodium hydroxide (2 ml, 4.0 mmol) and the reaction is heated to reflux for 1 hour. The reaction is then concentrated to dryness and the residue is dissolved in 95% dichloromethane/5% isopropanol and washed with 0.1N HCl. The organic layer is separated and dried over anhydrous sodium sulfate, filtered, and concentrated to provide 0.403 g (90%) of the pure title compound. MS (ES−) m/e 354.0 $(M-1)^-$.

Example 21

C-Phenyl-N-[4-(2-(S)-pyrrolidin-1-ylmethyl-pyrrolidine-1-carbonyl)-phenyl]-methanesulfonamide hydrochloride

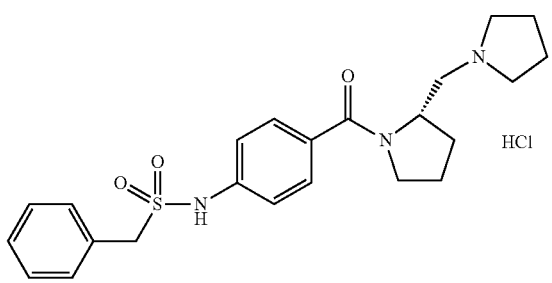

To a stirring solution of 4-phenylmethanesulfonylaminobenzoic acid (CAS 536-95-8, available from Aldrich) (0.300 g, 1.03 mmol), in dichloromethane (10 mL) is added oxalyl chloride (0.262 g, 2.06 mmol) and 1 drop of N,N-dimethylformamide and the mixture allowed to react at ambient temperature for 1 hour. The reaction is then concentrated to dryness. The residue is dissolved in toluene (10 mL) and concentrated again. The residue is dissolved in dichloromethane (6 mL) and added to a flask containing (S)(+)-1-(2-pyrrolidinylmethyl)pyrrolidine (0.154 g, 1.0 mmol) and N-methylmorpholine (0.111 g, 1.1 mmol) and stirred for 20 min. The reaction is diluted with dichloromethane and washed successively with a saturated solution of sodium bicarbonate and water. The organic layer is separated, dried over anhydrous sodium sulfate, filtered, and concentrated to a solid. The solid is dissolved in dichloromethane (1 mL) and 2:1 diethyl ether/hexane is added. The resultant solid is filtered and dried to give the pure free base of the title compound. The free base (0.021 g, 0.049 mmol) is dissolved in dichloromethane (1 ml) and 1M anhydrous HCl in diethyl ether (0.1 ml) is added to precipitate the desired title compound as a white solid. MS (ES+) m/e 428.2 (M+1)$^+$ (free base).

Example 22

4-Methanesulfonyl-N-[4-(2-(S)-pyrrolidin-1-ylmethyl-pyrrolidine-1-carbonyl)-phenyl]-benzenesulfonamide The title compound is prepared substantially in accordance with the procedure for the free base of C-Phenyl-N-[4-(2-(S)-pyrrolidin-1-ylmethyl-pyrrolidine-1-carbonyl)-phenyl]-methanesulfonamide hydrochloride (Example 21) using the title compound of Intermediate 8 (4-(4-methanesulfonyl-benzenesulfonylamino)-benzoic acid) (0.270 g, 0.761 mmol), oxalyl chloride (0.145 g, 1.14 mmol), 1 drop N,N-dimethylformamide, N-methylmorpholine (0.081 g, 0.8 mmol), and (S)(+)-1-(2-pyrrolidinylmethyl)pyrrolidine (0.115 g, 0.75 mmol) in a 1:1 mixture of dichloromethane/acetonitrile. The reaction is purified by radial chromatography to provide 0.338 g (90%) of the title compound as a white solid. MS (ES+) m/e 492.1 (M+1)$^+$.

Example 23

4-Methanesulfonyl-N-methyl-N-[4-(2-(S)-pyrrolidin-1-ylmethyl-pyrrolidine-1-carbonyl)-phenyl]-benzenesulfonamide hydrochloride

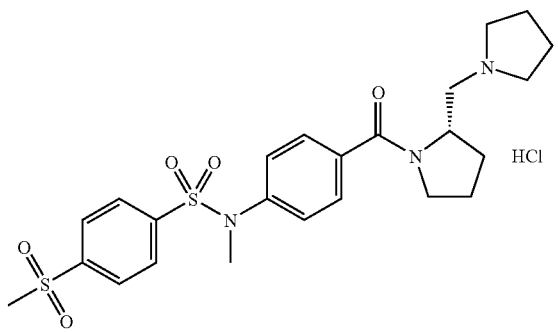

To a stirred solution of 4-methanesulfonyl-N-[4-(2-(S)-pyrrolidin-1-ylmethyl-pyrrolidine-1-carbonyl)-phenyl]-benzenesulfonamide (Example 22) (0.028 g, 0.057 mmol) in 2 ml dichloromethane (2 mL) is added 2 M (trimethylsilyl)diazomethane in hexane (0.063 ml, 0.126 mmol) and allowed to react for 5 hours at ambient temperature. The reaction is diluted with dichloromethane and washed with 0.1 N HCl. The organic layer are dried over anhydrous sodium sulfate, filtered, and concentrated to an oily solid. The oily solid is converted to the hydrochloride salt in accordance with the preparation of the title compound of Example 23 (C-Phenyl-N-[4-(2-pyrrolidin-1-ylmethyl-pyrrolidine-1-carbonyl)-phenyl]-methanesulfonamide; hydrochloride) to provide the title compound as a solid. MS (ES+) m/e 506.1 (M+1)$^+$.

Intermediate 9

Methanesulfonic acid 3-pyridin-4-yl-propyl ester

Procedure I

To a stirring solution of 3-pyridin-4-yl-propan-1-ol (0.71 mL, 5.47 mmol) in dichloromethane (20 mL) in a 0° C. ice bath, is added triethylamine (0.95 mL, 6.83 mmol) and methanesulfonylchloride (0.44 mL, 5.74 mmol) and the ice bath removed. The mixture is stirred at room temperature for 15 min after which time the reaction is complete. The product is left in solution and used as is in the subsequent reaction.

Intermediate 10

4-(3-Pyridin-4-yl-propylsulfanyl)-benzoic acid methyl ester

Procedure J

To a stirring solution of 4-mercapto-benzoic acid methyl ester (506 mg, 3.01 mmol) and potassium carbonate (1.245 g, 9.01 mmol) in dimethylformamide (10 mL), is added methanesulfonic acid 3-pyridin-4-yl-propyl ester (See Intermediate 14) in dicholoromethane (11 mL, 2.73 mmol). The dichloromethane is removed in vacuo and then the reaction is heated to 100° C. for 4 h. The reaction is allowed to cool to room temperature and washed with water while extracting with ethyl acetate. The organic portion is concentrated in vacuo. The resulting residue is purified using radial chromatography, eluting with methanol and dichloromethane to obtain 174 mg (22%) of the title compound. MS (ES+) m/e 288.1 (M+1)$^+$.

Intermediate 11

4-(3-Pyridin-4-yl-propylsulfanyl)-benzoic acid sodium salt

Procedure K

Heat a stirring solution of 4-(3-pyridin-4-yl-propylsulfanyl)-benzoic acid methyl ester (174 mg, 0.605 mmol) (Intermediate 10) and 2N sodium hydroxide (0.42 mL, 0.848 mmol) in 1:1 tetrahydrofuran/methanol (4 ml) to reflux temperature for 18 h. The reaction is allowed to cool and then concentrated in vacuo to obtain 180 mg (99%) of the title compound. MS (ES+) m/e 274.0 (M+1)+.

Intermediate 12

(4-Bromo-phenyl)-(2-(S)-pyrrolidin-1-ylmethyl-pyrrolidin-yl)methanone

Procedure L

To a stirring solution of 4-bromobenzoic acid-2,5-dioxopyrrolidin-1-yl ester (3.5 g, 11.7 mmol) [CAS: 80586-82-9] in tetrahydrofuran (0.15M), is added (S)-(+)-1-(2-pyrrolidinylmethyl)pyrrolidine (1.9 mL, 11.7 mmol) and the mixture heated to reflux for 4 h. The reaction is allowed to cool to room temperature and washed with water while extracting with 10% isopropanol/dichloromethane. The organic portion is dried with sodium sulfate, filtered, and concentrated in vacuo. The resulting residue is purified on a silica gel column, eluting with 2M ammonia in methanol and dichloromethane to obtain 2.80 g (71%) of the title compound. MS (ES+) m/e 337.1 (M+1)+.

Intermediate 13

N-(2-Pyridin-3-yl-ethyl)-terephthalamic acid methyl ester

Procedure M

To a stirring solution of terephthalic acid monomethyl ester (500 mg, 2.5 mmol) and oxalyl chloride (0.44 mL, 5.03 mmol) in dichloromethane (20 mL), is added 3 drops of dimethylformamide and the reaction is stirred for 2 h at room temperature. The reaction is concentrated in vacuo and then redissolved in dichloromethane. The solution is slowly added to a stirring solution of 3-(2-aminoethyl)pyridine (308 mg, 2.52 mmol) and n-methylmorpholine (0.28 mL, 2.52 mmol) in dichloromethane (20 mL). After 20 min, the reaction is washed with saturated aqueous sodium bicarbonate while extracting with 10% isopropanol/dichloromethane. The organic portion is dried with sodium sulfate, filtered, and concentrated in vacuo. The resulting residue is purified using radial chromatography, eluting with methanol and dichloromethane to obtain 613 mg (86%) of the title compound. MS (ES+) m/e 285.1 (M+1)+.

Intermediate 14

4-(Pyridin-3-ylsulfanyl)-benzoic acid

Procedure N

A mixture of 3-iodopyridine (823 mg, 4.01 mmol), methyl-4-mercaptobenzoate (500 mg, 2.97 mmol), potassium carbonate (677 mg, 4.90 mmol), and copper dust (4 mg, 0.653 mmol) in dimethylformamide (10 mL) are heated to reflux temperature for 18 h. The heat is removed and the reaction is filtered through Celite® with dichloromethane. The filtrate is concentrated in vacuo and the residue is recrystallized from ether and hexane to obtain 689 mg (99%) of the title compound. MS (ES+) m/e 232.0 (M+1)+.

Example 24

[4-(3-Pyridin-4-yl-propylsulfanyl)-phenyl]-(2-(S)-pyrrolidin-1-ylmethyl-pyrrolidin-1-yl)-methanone dihydrochloride

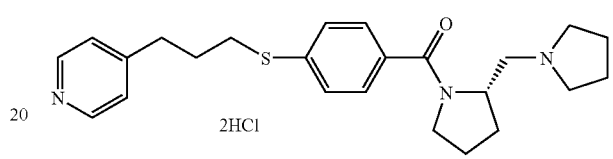

Procedure O

2-Chloro-4,6-dimethoxy-1,3,5-triazine (106 mg, 0.605 mmol) is added to a stirring solution of 4-(3-pyridin-4-yl-propylsulfanyl)-benzoic acid sodium salt (180 mg, 0.605 mmol) (Intermediate 11) and N-methyl morpholine (0.13 mL, 1.21 mmol) in dichloromethane (6 mL) in a 0° C. ice bath. The ice bath is removed and the reaction is stirred for 30 min. (S)-(+)-1-(2-pyrrolidinylmethyl)pyrrolidine (93 mg, 0.605 mmol) is added and stirring continued at room temperature for 18 h. The reaction is washed with saturated aqueous sodium bicarbonate while extracting with dichloromethane. The organic layer is dried with sodium sulfate, filtered, and concentrated in vacuo. The resulting residue is purified using silica gel chromatography, eluting with 2M ammonia in methanol and dichloromethane. The resulting free base is dissolved in a minimal amount of dichloromethane and 1M hydrochloric acid in ether is added until the solution becomes cloudy. Ether/hexanes (1/1) is added and the material concentrated in vacuo to yield 100 mg (34%) of the title compound. MS (ES+) m/e 410.3 (M+1)+.

Example 25

[4-(3-Pyridin-3-yl-propylsulfanyl)-phenyl]-(2-(S)-pyrrolidin-1-ylmethyl-pyrrolidin-1-yl)-methanone dihydrochloride

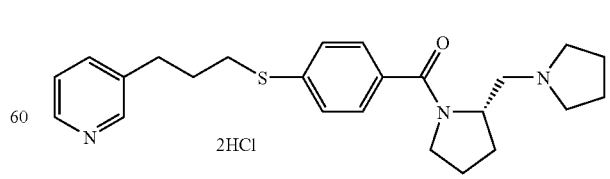

The title compound is prepared substantially in accordance with Procedures I through K, and Procedure O, starting with 3-pyridin-3-yl-propan-1-ol. MS (ES+) m/e 410.3 (M+1)+.

Example 26

[4-(Pyridin-4-ylsulfanyl)-phenyl]-(2-(S)-pyrrolidin-1-ylmethyl-pyrrolidin-1-yl)-methanone dihydrochloride

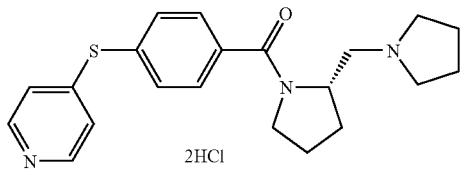

Procedure P

To a stirring solution of (4-bromo-phenyl)-(2-(S)-pyrrolidin-1-ylmethyl-pyrrolidin-yl)methanone (95 mg, 0.282 mmol) (See Intermediate 12), 4-mercaptopyridine (63 mg, 0.563 mmol) and copper bromide (8 mg, 0.563 mmol) in toluene, is added 1,8-diazabicyclo[5.4.0]undec-7-ene (0.08 mL, 0.563 mmol) and the reaction heated to reflux. After 2 h more copper bromide (80 mg, 5.63 mmol) is added and heating continued. This is repeated after two additional hours and reflux continued for 18 h. After this time, no product formation is observed. The reaction is concentrated in vacuo. Dimethylformamide (2 mL) and potassium carbonate (85 mg, 0.620 mmol) are added and the reaction heated to reflux for 48 h. The heat is removed and the reaction continued at room temperature for 48 h. The reaction is filtered through Celite® and then washed with water while extracting with ethyl acetate. The organic portion is concentrate in vacuo. The resulting residue is purified using radial chromatography eluting with 2M ammonia in methanol and dichloromethane. The resulting free base is dissolved in a minimal amount of dichloromethane and 1M hydrochloric acid in ether is added until the solution becomes cloudy. Ether/hexanes (1/1) is added and the material concentrated in vacuo to yield 34 mg (27%) of the title compound. MS (ES+) m/e 368.2 (M+1)+.

Example 27

N-(2-Pyridin-3-yl-ethyl)-4-(2-(S)-pyrrolidin-1-ylmethyl-pyrrolidine-1-carbonyl)-benzamide dihydrochloride

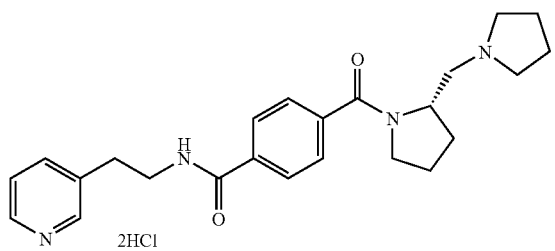

The title compound is prepared substantially in accordance with Procedures K and O starting with N-(2-pyridin-3-yl-ethyl)-terephthalamic acid methyl ester (Intermediate 13). MS (ES+) m/e 407.3 (M+1)+.

Example 28

[4-(Pyrimidin-4-ylsulfanyl)-phenyl]-(2-(S)-pyrrolidin-1-ylmethyl-pyrrolidin-1-yl)-methanone hydrochloride

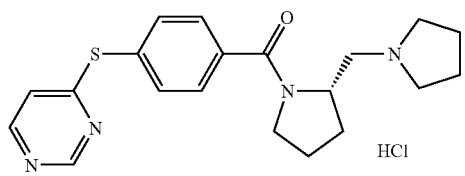

The title compound is prepared substantially in accordance with Procedure P starting with pyrimidine-4-thiol. MS (ES+) m/e 369.2 (M+1)+.

Example 29

[4-(Pyridin-3-ylsulfanyl)-phenyl]-(2-(S)-pyrrolidin-1-ylmethyl-pyrrolidin-1-yl)-methasone dihydrochloride

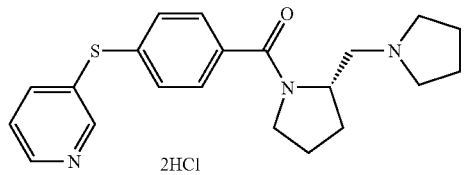

The title compound is prepared substantially in accordance with Procedure M starting with 4-(pyridin-3-ylsulfanyl)-benzoic acid (Intermediate 14). The resulting free base is dissolved in a minimal amount of dichloromethane and 1M hydrochloric acid in ether is added until the solution becomes cloudy. Ether/hexanes (1/1) is added and the material concentrated in vacuo to yield the salt. MS (ES+) m/e 368.2 (M+1)+.

The optimal time for performing the reactions of the Schemes, Preparations, and Procedures can be determined by monitoring the progress of the reaction via conventional chromatographic techniques. The skilled artisan will appreciate that not all substituents are compatible with all reaction conditions. These compounds may be protected or modified at a convenient point in the synthesis by methods well known in the art. (For example, see: Greene and Wuts, *Protective Groups in Organic Synthesis*, Third Edition, John Wiley and Sons Inc., 1999). Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

Preferably the compound is administered orally. Preferably, the pharmaceutical preparation is in a unit dosage form. In such form, the preparation is subdivided into suitably sized unit doses containing appropriate quantities of the active components, e.g., an effective amount to achieve the desired purpose. The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

The compositions of the invention may be formulated so as to provide quick, sustained or delayed release of the active ingredient after administration to the patient. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., eds., 19$^{th}$ ed., Mack Publishing Co., 1995).

Although a number of H3R antagonists are known in the art, none have proven to be satisfactory obesity or cognitive drugs. There is increasing evidence that histamine plays an important role in energy homeostasis. Histamine, acting as a neurotransmitter in the hypothalamus, suppressed appetite. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The compounds of the present invention can readily be evaluated by using a competitive inhibition Scintillation Proximity Assay (SPA) based on a H3R binding assay using [3H] a methylhistamine as ligand. Stable cell lines, including but not limited to HEK can be transfected with cDNA coding for H3R to prepare membranes used for the binding assay.

The technique is illustrated below (*Preparation of Histamine Receptor Subtype Membranes*) for the histamine receptor subtypes.

Membranes isolated as described in (*Preparation of Histamine Receptor Subtype Membranes*) are used in a [35S] GTPχS functional assay. Binding of [35S]GTPχS to membranes indicates agonist activity. Compounds of the invention of Formula I are tested for their ability to inhibit binding in the presence of agonists. Alternately, the same transfected cell lines are used for a cAMP assay wherein H3R agonists inhibited forskolin-activated synthesis of cAMP. Compounds of Formula I are tested for their ability to permit forskolin-stimulated cAMP synthesis in the presence of agonist.

A. Preparation H1R Membranes:

cDNA for the human histamine 1 receptor (H1R) is cloned into a mammalian expression vector containing the CMV promoter (pcDNA3.1(+), Invitogen) and transfected into HEK293 cells using the FuGENE Tranfection Reagent (Roche Diagnostics Corporation). Transfected cells are selected using G418 (500 µ/ml). Colonies that survived selection are grown and tested for histamine binding to cells grown in 96-well dishes using a scintillation proximity assay (SPA) based radioligand binding assay. Briefly, cells, representing individual selected clones, are grown as confluent monolayers in 96-well dishes (Costar Clear Bottom Plates, #3632) by seeding wells with 25,000 cells and growing for 48 hours (37° C., 5% $CO_2$). Growth media is removed and wells are rinsed two times with PBS (minus $Ca^{2+}$ or $Mg^{2+}$). For total binding, cells are assayed in a SPA reaction containing 50 mM Tris-HCL (assay buffer), pH 7.6, 1 mg wheat germ agglutinin SPA beads (Amersham Pharmacia Biotech, #RPNQ0001), and 0.8 nM $^3$H-pyrilamine (Net-594, NEN) (total volume per well=200 µl). Astemizole (10 µM, Sigma #A6424) is added to appropriate wells to determine non-specific binding. Plates are covered with FasCal and incubated at room temperature for 120 minutes. Following incubation, plates are centrifuged at 1,000 rpm (~800 g) for 10 minutes at room temperature. Plates are counted in a Wallac Trilux 1450 Microbeta scintillation counter. Several clones are selected as positive for binding, and a single clone (H1R40) is used to prepare membranes for binding studies. Cell pellets, representing ~10 grams, are resuspended in 30 ml assay buffer, mixed by vortexing, and centrifuged (40,000 g at 4° C.) for 10 minutes. The pellet resuspension, vortexing, and centrifugation is repeated 2 more times. The final cell pellet is resuspended in 30 ml and homogenized with a Polytron Tissue Homogenizer. Protein determinations are done using the Coomassie Plus Protein Assay Reagent (Pierce). Five micrograms of protein is used per well in the SPA receptor-binding assay.

B. Preparation H2R Membranes:

cDNA for the human histamine 2 receptor is cloned, expressed and transfected into HEK 293 cells as described above. Histamine binding to cells is assayed by SPA described above. For total binding, cells are assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM$^3$H-tiotidine (Net-688, NEN) (total volume per well=200 µl). Cimetidine (10 µM, Sigma #C4522) is added to appropriate wells to determine non-specific binding.

Several clones are selected as positive for binding, and a single clone (H2R10) is used to prepare membranes for binding studies. Five micrograms of protein is used per well in the SPA receptor-binding assay.

C. Preparation of H3R Membranes:

cDNA for the human histamine 3 receptor is cloned and expressed as described in (A. Preparation H1R membranes), above. Transfected cells are selected using G418 (500 µ/ml), grown, and tested for histamine binding by the SPA described above. For total binding, cells are assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM (3H)-n-alpha-methylhistamine (NEN, NET1027) (total volume per well=200 µl). Thioperimide is added to determine non-specific binding. Several clones are selected as positive for binding, and a single clone (H3R8) is used to prepare membranes for binding studies described above. Five micrograms of protein is used per well in the SPA receptor-binding assay.

The compounds according to the invention preferably have a Ki value of no greater than 5 µM as determined by the Histamine H3 Receptor Binding Assay disclosed herein. More preferably, the compounds according to the invention have a Ki value of less than 1 µM. All compounds set forth in the examples have a Ki for the H3 receptor of less than 1 µM. Preferably compounds of the invention have a Ki value of less than 500 nM and even more preferred of less than 100 nM as determined by the Histamine H3 Receptor Binding Assay disclosed herein. Most preferred compounds of the invention exhibit affinity for the H3 receptor greater than 20 nM. Furthermore, the compounds according to the invention preferably have a higher binding affinity to the histamine H3 receptor than to the GPRv53 receptor.

D. Preparation of GPRv53 Membranes cDNA for the human GPRv53 receptor is cloned and expressed as described in (A. Preparation H1R membranes), above. Transfected cells are selected, tested for histamine binding, and selected. HEK293 GPRv53 50 cells are grown to confluency in DMEM/F12 (Gibco) supplemented with 5% FBS and 500 µg/ml G418 and washed with Delbecco's PBS (Gibco) and harvested by scraping. Whole cells are homogenized with a Polytron tissuemizer in binding buffer, 50 mM Tris pH 7.5. Cell lysates, 50 ug, are incubated in 96 well dishes with 3 nM (3H) Histamine and compounds in binding buffer for 2 hours at room temperature. Lysates are filtered through glass fiber filters (Perkin Elmer) with a Tomtec cell harverster. Filters are counted with melt-on scintillator sheets (Perkin Elmer) in a Wallac Trilux 1450 Microbeta Scintillation counter for 5 minutes.

Pharmacological Results cAMP ELISA

HEK293 H3R8 cells prepared as described above are seeded at a density of 50,000 cells/well and grown overnight in DMEM/F12 (Gibco) supplemented with 5% FBS and 500 ug/ml G418. The next day tissue culture medium is removed and replaced with 50 µl cell culture medium containing 4 mM 3-isobutyl-1-methylxanthine (Sigma) and incubated for 20 minutes at room temperature. Antagonist are added in 50 µl cell culture medium and incubated for 20 minutes at room temperature. Agonist R(−)α methylhistamine (RBI) at a dose response from $1\times10^{-10}$ to $1\times10^{-5}$ M is then added to the wells in 50 µl cell culture medium and incubated for 5 minutes at room temperature. Then 50 µl of cell culture medium containing 20 µM Forskolin (Sigma) is added to each well and incubated for 20 minutes at room temperature. Tissue culture medium is removed and cells are lysed in 0.1M HCl and cAMP is measured by ELISA (Assay Designs, Inc.).

[35S] GTP γ [S] Binding Assay

Antagonist activity of selected compounds is tested for inhibition of [35S] GTP γ [S] binding to H3R membranes in the presence of agonists. Assays are run at room temperature in 20 mM HEPES, 100 mM NaCl, 5 mM $MgCl_2$ and 10 uM GDP at pH 7.4 in a final volume of 200 ul in 96-well Costar plates. Membranes isolated from H3R8-expressing HEK293 cell line (20 ug/well) and GDP are added to each well in a volume of 50 µl assay buffer. Antagonist is then added to the wells in a volume of 50 µl assay buffer and incubated for 15 minutes at room temperature. Agonist R(−)alpha methylhistamine (RBI) at either a dose response from $1\times10^{-10}$ to $1\times10^{-5}$ M or fixed concentration of 100 nM are then added to the wells in a volume of 50 µl assay buffer and incubated for 5 minutes at room temperature. GTP γ [35S] is added to each well in a volume of 50 µl assay buffer at a final concentration of 200 pM, followed by the addition of 50 µl of 20 mg/ml WGA coated SPA beads (Amersham). Plates are counted in Wallac Trilux 1450 Microbeta scintillation counter for 1 minute. Compounds that inhibited more than 50% of the specific binding of radioactive ligand to the receptor are serially diluted to determine a K[i](nM).

The Ki's at the human H3R are given below for the indicated compound.

TABLE 2

| Example | Ki (nM) |
|---|---|
| 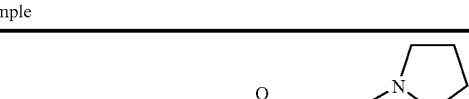 | 21.6 |
| 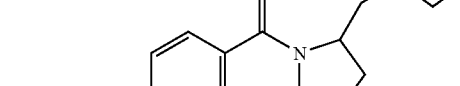 | 11.7 |

What is claimed:
1. A compound structurally represented by Formula I

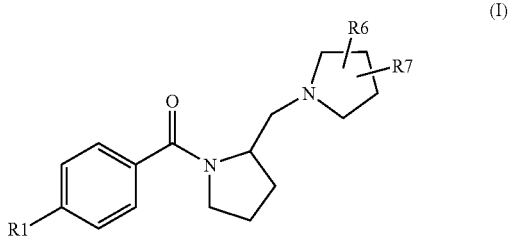

or a pharmaceutically acceptable salt thereof, wherein:
R1 is independently
—N(R2)SO$_2$-phenyl (wherein the phenyl is optionally substituted with R4), —N(R2)SO$_2$—CH$_2$-phenyl (wherein the phenyl is optionally substituted with R4), —SO$_2$N(R2)(R3), —SO$_2$—N-pyrrolidinyl (wherein the pyrrolidine is optionally substituted with R4), —SO$_2$—N-piperidinyl (wherein the piperidine is optionally substituted with R4), —SO$_2$—N-morpholinyl, or —X—(CH$_2$)$_n$—R5 (wherein X=S— and n is 0, 1, 2, 3, or 4); wherein when n is 0 then (CH$_2$)$_n$ is a bond;

R2 is independently —H or —($C_1$-$C_4$) alkyl(optionally substituted with one to three halogens);
R3 is independently
—($C_1$-$C_6$) alkyl(optionally substituted with one to three halogens), —($C_2$-$C_4$) alkylene-N-pyrrolidinyl, —($C_2$-$C_4$) alkylene-N-piperidinyl, —($C_2$-$C_4$) alkylene-N-morpholinyl, —($C_1$-$C_4$) allylene-2-pyridinyl, —($C_1$-$C_4$) alkylene-3-pyridinyl, or —($C_1$-$C_4$) alkylene-4-pyridinyl;
R4 is independently —$CH_3$, —$CF_3$, —CN, or —$SO_2CH_3$;
R5 is independently
-2-pyridinyl, -3-pyridinyl, -4-pyridinyl, -2-pyrimidinyl, or -4-pyrimidinyl;
R6 is independently —H or —($C_1$-$C_3$) alkyl(optionally substituted with one to three halogens); and
R7 is independently —H or —($C_1$-$C_3$) alkyl (optionally substituted with one to three halogens).

2. A compound or salt of claim 1 wherein R1 is —N(R2)$SO_2$-phenyl (wherein the phenyl is optionally substituted with R4), —N(R2)$SO_2$(—$CH_2$-phenyl) (wherein the phenyl is optionally substituted with R4).

3. A compound or salt of claim 1 wherein R1 is —$SO_2$N(R2)(R3), —$SO_2$—N-pyrrolidinyl (wherein the pyrrolidine is optionally substituted with R4), —$SO_2$—N-piperidinyl (wherein the piperidine is optionally substituted with R4), or —$SO_2$—N-morpholinyl.

4. A compound or salt of claim 1 wherein R1 is —S($CH_2$)$_n$—R5 (wherein n is 0, 1, 2, 3, or 4), wherein when n is 0 then ($CH_2$)$_n$ is a bond.

5. The compound or salt of claim 1 wherein R1 is independently —$SO_2$—N(—$CH_2CH_3$)(—$CH_2CH_3$); —$SO_2$—N-pyrrolidinyl; —$SO_2$—N-morpholinyl; —$SO_2$—N-pyrrolidinyl-3-$SO_2CH_3$; —N(H)(—$SO_2$—$CH_2$-phenyl); —N(H)(—$SO_2$-phenyl-4-$SO_2CH_3$); —N(—$CH_3$)(—$SO_2$-phenyl-4-$SO_2CH_3$); —S—$CH_2$—$CH_2$—$CH_2$-4-pyridinyl; —S—$CH_2$—$CH_2$—$CH_2$-3-pyridinyl; —S-4-pyridinyl; —S-4-pyrimidinyl; or —S-3-pyridinyl.

6. A compound or salt of claim 1 wherein R6 and R7 are independently —H or —$CH_3$.

7. The compound or salt of claim 1 wherein R6 is —$CH_3$ and R7 is —H.

8. The compound or salt of claim 1, wherein R6 is —H and R7 is —H.

9. The compound of claim 1, selected from the group consisting of formulae X7, X17 to X25, X27 and X28:

| Formula Number | Structure |
| --- | --- |
| X7 | 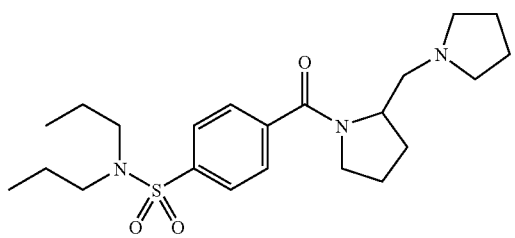 |
| X17 | 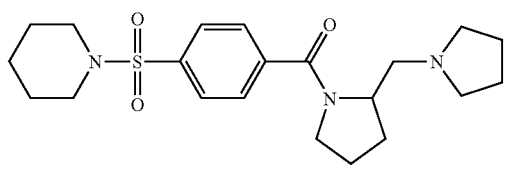 |
| X18 | 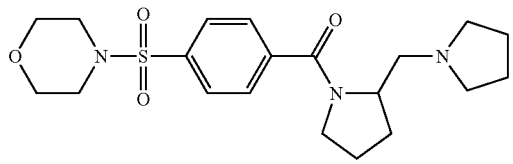 |
| X19 | 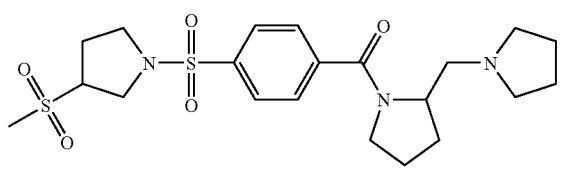 |

-continued
| Formula Number | Structure |
|---|---|
| X20 | 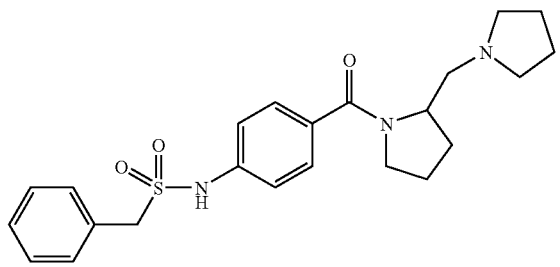 |
| X21 | 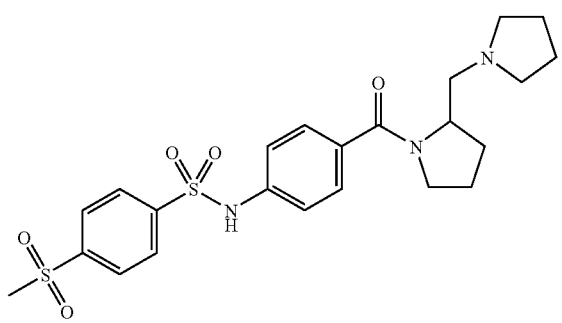 |
| X22 | 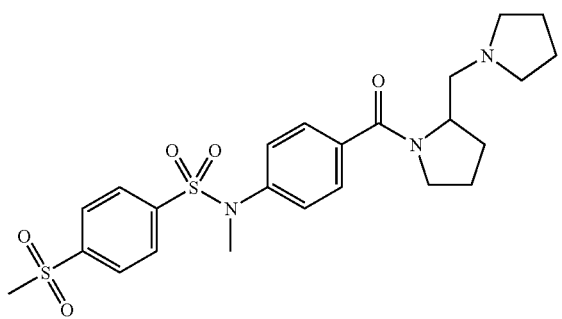 |
| X23 | 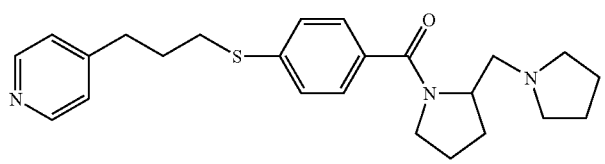 |
| X24 | 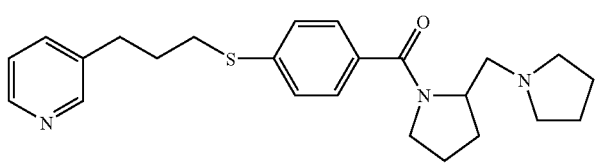 |
| X25 | 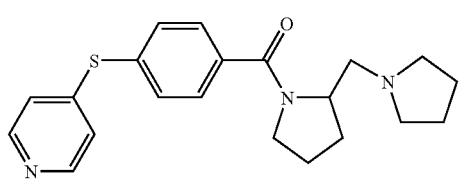 |

| Formula Number | Structure |
|---|---|
| X27 | 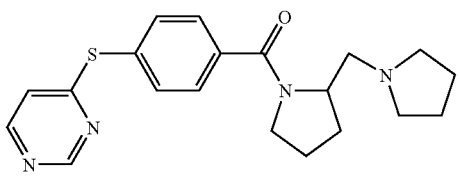 |
| X28 | 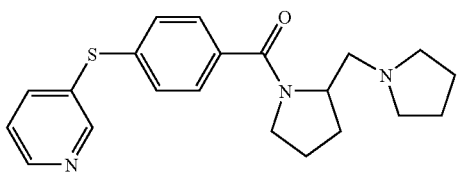 | or a pharmaceutically acceptable salt thereof.

10. The compound of claim 1 selected from the group consisting of:

N,N-Dipropyl-4-(2-(S)-pyrrolidin-1-ylmethyl-pyrrolidine-1-carbonyl)-benzenesulfonamide;

[4-(piperidine-1-sulfonyl)-phenyl]-(2-(S)-pyrrolidin-1-ylmethyl-pyrrolidin-1-yl)-methanone;

[4-(Morpholine-4-sulfonyl)-phenyl]-(2-(S)-pyrrolidin-1-ylmethyl-pyrrolidin-1-yl)-methanone;

[4-(3-Methanesulfonyl-pyrrolidine-1-sulfonyl)-phenyl]-(2-(S)-pyrrolidin-1-ylmethyl-pyrrolidin-1-yl)-methanone;

C-Phenyl-N-[4-(2-(S)-pyrrolidin-1-ylmethyl-pyrrolidine-1-carbonyl)-phenyl]-methanesulfonamide;

4-Methanesulfonyl-N-[4-(2-(S)-pyrrolidin-1-ylmethyl-pyrrolidine-1-carbonyl)-phenyl]-benzenesulfonamide;

4-Methanesulfonyl-N-methyl-N-[4-(2-(S)-pyrrolidin-1-ylmethyl-pyrrolidine-1-carbonyl)-phenyl]-benzenesulfonamide;

[4-(3-Pyridin-4-yl-propylsulfanyl)-phenyl]-(2-(S)-pyrrolidin-1-ylmethyl-pyrrolidin-1-yl)-methanone;

[4-(3-Pyridin-3-yl-propylsulfanyl)-phenyl]-(2-(S)-pyrrolidin-1-ylmethyl-pyrrolidin-1-yl)-methanone;

[4-(Pyridin-4-ylsulfanyl)-phenyl]-(2-(S)-pyrrolidin-1-ylmethyl-pyrrolidin-1-yl)-methanone;

[4-(Pyrimidin-4-ylsulfanyl)-phenyl]-(2-(S)-pyrrolidin-1-ylmethyl-pyrrolidin-1-yl)-methanone; and

[4-(Pyridin-3-ylsulfanyl)-phenyl]-(2-(S)-pyrrolidin-1-ylmethyl-pyrrolidin-1-yl)-methanone;

or a pharmaceutically acceptable salt thereof.

11. A pharmaceutical composition which comprises a compound or salt of claim 1 and a pharmaceutically acceptable carrier.

* * * * *